(12) United States Patent
Imura

(10) Patent No.: US 8,288,739 B2
(45) Date of Patent: Oct. 16, 2012

(54) METHOD AND APPARATUS FOR MEASURING OPTICAL PROPERTY OF FLUORESCENT SAMPLE

(75) Inventor: Kenji Imura, Toyohashi (JP)

(73) Assignee: Konica Minolta Sensing, Inc., Osaka (JP)

( * ) Notice: Subject to any disclaimer, the term of this patent is extended or adjusted under 35 U.S.C. 154(b) by 737 days.

(21) Appl. No.: 12/381,926

(22) Filed: Mar. 18, 2009

(65) Prior Publication Data

US 2009/0242803 A1    Oct. 1, 2009

(30) Foreign Application Priority Data

Mar. 25, 2008  (JP) ................................. 2008-078868

(51) Int. Cl.
*F21V 9/16* (2006.01)
(52) U.S. Cl. ................ 250/461.1; 250/458.1; 250/459.1
(58) Field of Classification Search ............... 250/458.1, 250/459.1, 461.1
See application file for complete search history.

(56) References Cited

U.S. PATENT DOCUMENTS

| | | | |
|---|---|---|---|
| 5,636,015 A | 6/1997 | Imura et al. | |
| 6,278,521 B1 * | 8/2001 | Jablonski et al. | 356/402 |
| 7,675,620 B2 * | 3/2010 | Imura | 356/402 |
| 7,847,264 B2 * | 12/2010 | Wegmuller et al. | 250/372 |
| 2006/0227319 A1 | 10/2006 | Imura | |
| 2007/0086009 A1 * | 4/2007 | Ehbets et al. | 356/402 |
| 2009/0097028 A1 * | 4/2009 | Vogh, Jr. | 356/407 |

FOREIGN PATENT DOCUMENTS

| | | |
|---|---|---|
| JP | 08-313349 A | 11/1996 |
| JP | 2006-292510 A | 10/2006 |

OTHER PUBLICATIONS

Zwinkels, Joanne, "Surface Fluorescence: The Only Standardized Method of Measuring Luminescence," Mar. 20, 2008, Springer Ser Fluoresc, col. 5, pp. 163-192.*
FIGS. 9 and 10 of present application entitled "Method and Apparatus for Measuring Optical Property of Fluorescent Sample,".

* cited by examiner

*Primary Examiner* — Christine Sung
(74) *Attorney, Agent, or Firm* — Brinks Hofer Gilson & Lione

(57) ABSTRACT

An optical property measuring method and an optical property measuring apparatus according to an aspect of the invention are operable to select bi-spectral characteristics relatively close to bi-spectral characteristics of a fluorescent sample, out of multiple bi-spectral characteristics stored in advance, based on a relative ratio between excitation efficiencies of the fluorescent sample illuminated by excitation illuminations whose spectral distributions are different from each other, in calculating an optical property of the fluorescent sample. The inventive optical property measuring method and optical property measuring apparatus are advantageous in calculating an optical property of a fluorescent sample easily and with high precision.

9 Claims, 10 Drawing Sheets

METHOD AND APPARATUS FOR MEASURING OPTICAL PROPERTY OF FLUORESCENT SAMPLE

This application is based on Japanese Patent Application No. 2008-78868 filed on Mar. 25, 2008, the contents of which are hereby incorporated by reference.

BACKGROUND OF THE INVENTION AND RELATED ART STATEMENT

1. Field of the Invention

The present invention relates to a method and apparatus for measuring an optical property of a fluorescent sample such as a sample treated with a fluorescent whitening agent (hereinafter, also called as "FWA treated sample"), and a printed sample on a substrate treated with a fluorescent whitening agent (hereinafter, also called as "FWA treated substrate").

2. Description of the Related Art

In recent years, many of the products such as paper and fabrics are treated with a fluorescent whitening agent. It is impossible to evaluate whiteness or color of the products and articles using the products as a substrate, without considering an influence of fluoresced light. Accordingly, it is necessary to solve the problem in technical fields related to these products and articles. Specifically, if UV light which is invisible to human eyes is absorbed by a fluorescent substance, the fluorescent substance is excited, and visible light in a longer wavelength band is radiated from the fluorescent substance. Since a degree of excitation (fluorescent intensity) differs depending on a light source, appearance of an identical measurement sample may differ depending on the light source. In view of the above circumstances, there is a demand for improvement in colorimetry for FWA treated paper and fabric, and printed samples on an FWA treated substrate.

Generally, a visible property i.e. an optical property of a reflecting sample is expressed by a ratio relative to white. Specifically, the optical property of a reflecting sample is expressed based on a total spectral radiance factor $B(\lambda)$. The total spectral radiance factor $B(\lambda)$ is a ratio of light emitted from a reflecting sample illuminated in a certain illuminating condition and received in a certain receiving condition to light emitted from a perfect reflecting diffuser in the identical illuminating and receiving conditions at each wavelength $\lambda$.

As described above, fluoresced light emitted by excitation light is superimposed over reflecting light on a sample (hereinafter, called as a "fluorescent sample") such as an FWA treated sample or a printed sample on an FWA treated substrate, and the color of the fluoresced light is observed as an objective light. In other words, radiation from a fluorescent sample is the sum of reflecting light (reflection component) and fluoresced light (fluorescent component) from the fluorescent sample. Accordingly, the total spectral radiance factor $B(\lambda)$ of a fluorescent sample is given, in the similar manner as described above, as the sum of a reflection spectral radiance factor $R(\lambda)$ and a fluorescent spectral radiance factor $F(\lambda)$. The reflection spectral radiance factor $R(\lambda)$ is a ratio of reflecting light from a fluorescent sample illuminated in a certain illuminating condition and received in a certain receiving condition to light emitted from a perfect reflecting diffuser in the identical illuminating and receiving conditions; and the fluorescent spectral radiance factor $F(\lambda)$ is a ratio of fluoresced light emitted from the fluorescent sample illuminated in the certain illuminating condition and received in the certain receiving condition to light emitted from the perfect reflecting diffuser in the identical illuminating and receiving conditions. The total spectral radiance factor $B(\lambda)$ is expressed by the Equation (1).

$$B(\lambda)=R(\lambda)+F(\lambda) \quad (1)$$

Since the perfect reflecting diffuser has no fluorescence, and the reflectivity thereof has no dependence on the wavelength of illumination, the total spectral radiance factor $B(\lambda)$, the reflection spectral radiance factor $R(\lambda)$, and the fluorescent spectral radiance factor $F(\lambda)$ are equivalent to the ratios of light of the wavelength $\lambda$ emitted, reflected and fluoresced from the sample respectively to the illumination of the same wavelength $\lambda$ except for a proportional coefficient. An object of the colorimetry is to obtain a measurement value analogous to visual observation. In the case where a fluorescent sample having an objective color is measured, the total spectral radiance factor $B(\lambda)$ is a measurement value to be obtained, and colorimetric values are derived from the total spectral radiance factor $B(\lambda)$.

CIE (International Committee of Illumination) defines spectral distributions (spectral intensities) of illumination for colorimetry such as Illuminant D65 (day light) and Illuminant A (incandescent light source), as well as standard illuminations such as Illuminants D50, D75, F11, and C. For measurement of fluorescent samples, standard illuminations such as Illuminants C and D50 are generally used. The fluorescent characteristics of a fluorescent sample or a fluorescent substance illuminated by the illumination are expressed by a bi-spectral luminescent radiance factor $F(\mu,\lambda)$. The bi-spectral luminescent radiance factor is matrix data showing the intensity of fluoresced light of the wavelength $\lambda$ excited by excitation light i.e. incident light of the wavelength $\mu$ for illuminating a fluorescent sample surface with a unit intensity i.e. by monochromatic light of a unit intensity.

An example of the matrix data is shown in FIG. 8. The matrix data is three-dimensional data, wherein the fluorescent wavelength $\lambda$ (unit: nm) and the excitation wavelength $\mu$ (unit: nm) are defined in x-axis and y-axis, respectively, and the fluorescent intensity is defined in z-axis. As is obvious from the matrix data, a section (e.g. a section where $\lambda$ is 550 nm) taken along a specific fluorescent wavelength $\lambda$ represents a spectral excitation efficiency i.e. an excitation efficiency of excitation light for exciting fluoresced light of the wavelength $\lambda$ at each wavelength. A section (e.g. a section where $\mu$ is 450 nm) taken along a specific excitation wavelength $\mu$ represents a spectral intensity of fluoresced light excited by an illumination of 450 nm. Accordingly, in a sense, a fluorescent phenomenon is a phenomenon involving a wavelength conversion from the wavelength $\mu$ to the wavelength $\lambda$. Therefore, a fluorescent spectral radiance factor $F(\lambda)$ of a fluorescent sample having a bi-spectral luminescent radiance factor $F(\mu,\lambda)$ is expressed by the Equation (2), where the proportional coefficient is neglected, when illuminated by an illumination I having a spectral distribution $I(\mu)$.

$$F(\lambda)=\int F(\mu,\lambda) \cdot I(\mu) d\mu / I(\lambda) \quad (2)$$

Specifically, the fluorescent spectral radiance factor $F(\lambda)$ is obtained as the ratio of convolution of the spectral distribution $I(\mu)$ of the illumination I and the bi-spectral luminescent radiance factor $F(\mu,\lambda)$ to the spectral distribution $I(\lambda)$ of the illumination I. The spectral distribution $I(\lambda)$ of the illumination I is substantially equivalent to reflections from the perfect reflecting diffuser (plane), except for the proportional coefficient. In the Equations throughout the specification, the symbols "·", "/", and "∫" represent multiplication, division, and integration, respectively.

As indicated by the Equation (2), the fluorescent spectral radiance factor $F(\lambda)$ depends on the spectral distribution $I(\mu)$ of the illumination I. Accordingly, the total spectral radiance factor $B(\lambda)$, which is the sum of the fluorescent spectral radiance factor $F(\lambda)$ and the reflection spectral radiance factor $R(\lambda)$ which itself has no dependence on the spectral distribution $I(\mu)$ of the illumination I also depends on the spectral distribution $I(\mu)$. In other words, the total spectral radiance factor $B(\lambda)$ to be measured based on $R(\lambda)$ and $F(\lambda)$, and calorimetric values derived from the total spectral radiance factor $B(\lambda)$ are different depending on a difference in spectral distribution of illumination with respect to a fluorescent sample.

Accordingly, it is required to specify a spectral distribution of a certain illumination (hereinafter, illumination for use in evaluating an optical property such as $F(\lambda)$ and $B(\lambda)$ is called as "test illumination") in evaluating an optical property of a fluorescent sample. In actual measurement, the spectral distribution of illumination of a measuring apparatus need to match with the spectral distribution of the specific test illumination. However, it is difficult to match the spectral distribution of illumination of a measuring apparatus with the spectral distribution of the specific test illumination, in other words, to obtain an illumination having the same spectral distribution as the spectral distribution of the standard illumination (such as the illuminant D50 or C) generally used as the test illumination.

There is proposed another approach of numerically calculating the fluorescent spectral radiance factor $F(\lambda)$ or the total spectral radiance factor $B(\lambda)$, using the Equation (2) by measuring a bi-spectral luminescent radiance factor $F(\mu,\lambda)$ or a bi-spectral radiance factor $B(\mu,\lambda)$, and based on the measured bi-spectral luminescent radiance factor $F(\mu,\lambda)$ or bi-spectral radiance factor $B(\mu,\lambda)$, and a spectral distribution $I(\lambda)$ of a test illumination given as numerical data. Here, similarly to the bi-spectral luminescent radiance factor $F(\mu,\lambda)$, the bi-spectral radiance factor $B(\mu,\lambda)$ is matrix data showing an intensity of the total emission of the wavelength $\lambda$ which is the sum of fluoresced light of the wavelength $\lambda$ and reflecting light by an illumination of the wavelength $\mu$ for illuminating a fluorescent sample surface with a unit intensity. The total spectral radiance factor $B(\mu,\lambda)$ is obtained as a ratio of convolution of a spectral distribution $I(\mu)$ of an illumination I and a bi-spectral radiance factor $B(\mu,\lambda)$ to $I(\lambda)$.

$$B(\lambda)=\int B(\mu,\lambda)\cdot I(\mu)d\mu/I(\lambda) \qquad (3)$$

However, measurement of the bi-spectral luminescent radiance factor $F(\mu,\lambda)$ or the bi-spectral radiance factor $B(\mu,\lambda)$ (hereinafter, the two radiance factors are generically called as "bi-spectral characteristics"; and the fluorescent spectral radiance factor $F(\lambda)$ and the total spectral radiance factor $B(\lambda)$ to be individually calculated are generically called as "spectral fluorescent characteristics") requires a complicated and time-consuming bi-spectro-fluorometer e.g. a double monochromator comprising two spectral units, one for illumination and the other for receiving. Accordingly, use of the bi-spectro-fluorometer is not practical. Quality control of products such as FWA treated paper as a representative example of a fluorescent sample is generally performed using one of the following two simplified methods.

(Gaertner and Griesser's Method)

In this section, Gaertner and Griesser's method is described as a first approach. As shown in FIG. 9, a fluorescent sample 601 is placed at a sample aperture 603 of an integrating sphere 602 of an optical property measuring apparatus 600. A light flux 605 emitted from a light source 604 such as a xenon flash lamp having a sufficient spectral intensity in a UV region enters into the integrating sphere 602 through an aperture of the integrating sphere 602. A UV cut filter 606 is inserted at such a position as to partially block the optical path of the light flux 605 to remove a UV component from a part of the light flux 605 which passes through the UV cut filter 606. The degree of insertion of the UV cut filter 606 is adjustable so as to allow adjustment of a ratio (relative UV intensity) of intensity of an illumination in a UV region (excitation region) to that of the illumination in a visible region. Both a part of the light flux 605 that has passed through the UV cut filter 606 and a part of the light flux 605 that has not passed through the UV cut filter 606 enter into the integrating sphere 602 and undergo multiple diffuse reflections within the integrating sphere 602, and form illumination for illuminating the fluorescent sample 601.

A component (radiation component 607) of light emitted in a predetermined direction from the surface of the fluorescent sample 601 illuminated by the illumination enters a sample spectral unit 608 for measuring a spectral distribution $Sx(\lambda)$ of the radiation component 607. Similarly, a light flux 609 having substantially the same spectral distribution as that of the illumination directly enters a monitoring optical fiber 610 so as to be directed to a monitoring spectral unit 611 for measuring a spectral distribution $Mx(\lambda)$ of the light flux 609. A computation controller 612 calculates a total spectral radiance factor $Bx(\lambda)$ based on measurement information on the spectral distribution $S(\lambda)$ of the radiation component 607 and the spectral distribution $Mx(\lambda)$ of the light flux 609.

Calibration of the relative UV intensity is performed as follows. Specifically, a fluorescent standard containing a fluorescent substance having excitation-fluorescent characteristics, namely, a bi-spectral luminescent radiance factor close to that of the fluorescent sample 601, and whose calorimetric value (e.g. whiteness WIs defined by the CIE) under a specific test illumination is known is used. The fluorescent standard is placed at the sample aperture 603. Then, a total spectral radiance factor $B(\lambda)$ is measured by the optical property measuring apparatus 600. Then, the degree of insertion of the UV cut filter 606 is adjusted to match a whiteness WI calculated based on the total spectral radiance factor $B(\lambda)$ with the known whiteness WIs.

The Gaertner and Griesser's method is mechanically complicated and unreliable, and also requires complicated and time-consuming calibration, in other words, measurements and adjustments of the UV cut filter 606 need to be repeated until the whiteness WI agrees with the known whiteness WIs. Also, the above method has the degree of freedom "1". Accordingly, it is fundamentally impossible to simultaneously calibrate two or more calorimetric values such as the whiteness WI and Tint value, or perform calibration to match the total spectral radiance factor $B(\lambda)$ with a total spectral radiance factor $Bs(\lambda)$ to be obtained in the case where a fluorescent sample is illuminated by a known test illumination.

(Method of JP Hei 8-313349A Corresponding to U.S. Pat. No. 5,636,015)

In this section, the method recited in JP Hei 8-313349A corresponding to U.S. Pat. No. 5,636,015 (D1) is described as a second approach. The measurement method recited in D1 is substantially the same, in principle, as the Gaertner and Griesser's method in that illuminations are combined depending on a degree of insertion of the UV cut filter 606 to numerically synthesize the total spectral radiance factor $Bx(\lambda)$. The degree of freedom is also "1" in D1. The measurement method in D1 is different from the Gaertner and Griesser's method in that the measurement method in D1 comprises adjusting a relative UV intensity at each wavelength $\lambda$, numerically synthesizing the total spectral radiance factor B(λ) first, and synthesizing an illumination that gives the total spectral radiance factor B(λ) as a result.

More specifically, an optical property measuring apparatus 700 shown in FIG. 10 is provided with an integrating sphere 702, a first illuminator 704 for emitting a light flux 703 having a UV intensity, a second illuminator 706 for emitting a light flux 705 having no UV intensity, a sample spectral unit 709 for measuring a spectral distribution of light (radiation component 708) emitted from a fluorescent sample 701 placed at a sample aperture 707, a monitoring spectral unit 712 for measuring a spectral distribution of a light flux 710 of illuminations through an optical fiber 711, and a computation controller 713.

In the optical property measuring apparatus 700, the fluorescent sample 701 is illuminated by the first and the second illuminators 704 and 706, and spectral distributions Sx1(λ) and Sx2(λ) of radiations from the fluorescent sample 701, and spectral distributions Mx1(λ) and Mx2(λ) of illuminations are respectively measured. Total spectral radiance factors Bx1(λ) and Bx2(λ) of the fluorescent sample 701 illuminated by the illuminations from the first and the second illuminators 704 and 706 are obtained based on the spectral distributions Sx1(λ) and Sx2(λ) of radiations, and the spectral distributions Mx1(λ) and Mx2(λ) of illuminations. Thereafter, a total spectral radiance factor Bxc(λ) is obtained by linearly combining the total spectral radiance factors Bx1(λ) and Bx2(λ) weighted with a weighting factor W(λ) (hereinafter, also called as a "weight") stored in advance at each wavelength, as expressed by the Equation (4).

$$Bxc(\lambda)=W(\lambda)\cdot Bx1(\lambda)+(1-W(\lambda))\cdot Bx2(\lambda) \quad (4)$$

The total spectral radiance factor Bxc(λ) is defined as a total spectral radiance factor of the fluorescent sample 701 illuminated by the test illumination.

Similarly to the Gaertner and Griesser's method, the weighting factor W(λ) has a fluorescent characteristic close to a fluorescent characteristic of the fluorescent sample 701, and is determined using a fluorescent standard having a known total spectral radiance factor BS(λ) when illuminated by a test illumination. Specifically, the weighting factor W(λ) is numerically calculated at each wavelength by matching a value of (W(λ)·B1(λ)+(1−W(λ))·B2(λ)) obtained by linearly combining a total spectral radiance factor B1(λ) measured by illuminating the fluorescent standard by the first illuminator 704, and a total spectral radiance factor B2(λ) measured by illuminating the fluorescent standard by the second illuminator 706, with the weighting factor W(λ), with the known total spectral radiance factor Bs(λ) (see e.g. FIG. 2 in D1).

The above method is substantially equivalent to numerically calibrating the relative UV intensity by the Gaertner and Griesser's method, using the total spectral radiance factor B(λ) as a parameter, at each wavelength. Since the method is directed to calibrating the total spectral radiance factor B(λ), the method has an advantage that all the calorimetric values derived from the total spectral radiance factor B(λ) are calibrated. The above method eliminates many shortcomings of the Gaertner and Griesser's method, because an operation of a mechanical movable member, and a cumbersome adjustment of an insertion degree of the UV cut filter 606 in measurement are not necessary. However, both of the first and the second approaches still require a fluorescent standard, and calibration prior to measurement, using the fluorescent standard. Therefore, error resulting from displacement of a light source after calibration is unavoidable. Also, since a fluorescent substance contained in the fluorescent standard is composed of an organic material, the fluorescent standard needs to be replaced about once a month, in view of deterioration of the fluorescent standard.

In view of the above, the inventor of the present application proposed another approach, as disclosed in JP 2006-292510 corresponding to US 2006-227319A1 (D2). In the measurement method in D2, a fluorescent sample "x" having bi-spectral characteristics close to specific bi-spectral characteristics expressed by a predetermined bi-spectral luminescent radiance factor is illuminated by two illuminations I1 and I2 both having a spectral intensity in a visible region, and different relative intensities between an excitation region and a fluorescent region. Then, total spectral radiance factors Bx1(λ) and Bx2(λ) are measured, and spectral distributions I1(μ) and I2(μ) of the illuminations I1 and I2 are measured. Then, as shown by the Equations (5) through (7), fluorescent spectral radiance factors F1(λ), F2(λ), and Fs(λ) by the illuminations I1, I2, and a specific test illumination Is are numerically calculated, using the measured spectral distributions I1(μ) and I2(μ) of the illuminations I1 and I2, a spectral distribution Is(μ) of the test illumination Is which is given as data in advance, and the aforementioned predetermined bi-spectral luminescent radiance factor F(μ,λ)

$$F1(\lambda)=\int F(\mu,\lambda)\cdot I1(\mu)d\mu/I1(\lambda) \quad (5)$$

$$F2(\lambda)=\int F(\mu,\lambda)\cdot I2(\mu)d\mu/I2(\lambda) \quad (6)$$

$$Fs(\lambda)=\int F(\mu,\lambda)\cdot Is(\mu)d\mu/Is(\lambda) \quad (7)$$

Here, the weighting factors W(λ) and 1−W(λ) are determined so that the fluorescent spectral radiance factor Fs(λ) by the test illumination Is is expressed by a weighted linear combination obtained by linearly combining the fluorescent spectral radiance factors F1(λ) and F2(λ) by the illuminations I1 and I2, weighted with the weighting factors W(λ) and 1−W(λ), as expressed by the Equation (8).

$$Fs(\lambda)=W(\lambda)\cdot F1(\lambda)+(1-W(\lambda))\cdot F2(\lambda) \quad (8)$$

As expressed by the Equation (1), the total spectral radiance factor B(λ) is the sum of the fluorescent spectral radiance factor F(λ), and the reflection spectral radiance factor R(λ) which has no dependence on a spectral distribution of illumination. Accordingly, the weighting factors W(λ) and 1−W(λ) expressed in the Equation (8) can be also applied to the measured total spectral radiance factors Bx1(λ) and Bx2(λ). Thereby, a total spectral radiance factor Bxc(λ) close to a total spectral radiance factor Bxs(λ) of the fluorescent sample illuminated by the specific test illumination can be calculated, using the Equation (9).

$$Bxc(\lambda)=W(\lambda)\cdot Bx1(\lambda)+(1-W(\lambda))\cdot Bx2(\lambda) \quad (9)$$

In the above approach, the weighting factors W(λ) and 1−W(λ) are determined based on the fluorescent spectral radiance factor F(λ) using the bi-spectral luminescent radiance factor F(μ,λ). Alternatively, the weighting factors W(λ) and 1−W(λ) may be determined based on a total spectral radiance factor B(λ) using a bi-spectral radiance factor B(μ,λ).

The method of D2 is advantageous in measuring an optical property of FWA treated paper or a printed sample on FWA treated paper, without using a fluorescent standard or performing calibration using a fluorescent standard. However, similarly to the Gaertner and Griesser's method and the method of D1, which are performed based on a premise that excitation-fluorescent characteristics are close to each other between a fluorescent sample and a fluorescent standard, the method of D2 is performed based on a premise that bi-spectral characteristics (in the following section corresponding to a bi-spectral luminescent radiance factor $F(\mu,\lambda)$) of FWA treated paper as a sample are close to a predetermined bi-spectral luminescent radiance factor to be used in calculation. Therefore, if the bi-spectral luminescent radiance factor $F(\mu, \lambda)$ is not close to the predetermined bi-spectral luminescent radiance factor to be used in calculation, an error may be increased. As described above, since measurement of a bi-spectral luminescent radiance factor $F(\mu,\lambda)$ of a sample requires a bi-spectro-fluorometer, the measurement is generally difficult. As practical means equivalent to the method using a bi-spectro-fluorometer, there is proposed an idea of allowing a user to select a bi-spectral luminescent radiance factor close to the bi-spectral luminescent radiance factor $F(\mu,\lambda)$ of a sample, out of multiple bi-spectral luminescent radiance factors stored in advance. However, letting a user to select a bi-spectral luminescent radiance factor imparts a load to the user. Also, since the bi-spectral characteristics of samples are generally not disclosed to the public, the probability of error by erroneous selection is likely to be increased.

SUMMARY OF THE INVENTION

In view of the above, it is an object of the present invention to provide an optical property measuring method and an optical property measuring apparatus that enable to obtain an optical property of a fluorescent sample easily and with high precision.

An optical property measuring method and an optical property measuring apparatus according to an aspect of the invention are operable to select bi-spectral characteristics relatively close to bi-spectral characteristics of a fluorescent sample, out of multiple bi-spectral characteristics stored in advance, based on a relative ratio between excitation efficiencies of the fluorescent sample illuminated by excitation illuminations whose spectral distributions are different from each other, in calculating an optical property of the fluorescent sample. The inventive optical property measuring method and optical property measuring apparatus are advantageous in calculating an optical property of a fluorescent sample easily and with high precision.

These and other objects, features and advantages of the present invention will become more apparent upon reading the following detailed description along with the accompanying drawings.

DETAILED DESCRIPTION OF THE PREFERRED EMBODIMENTS OF THE INVENTION

Figure 1:
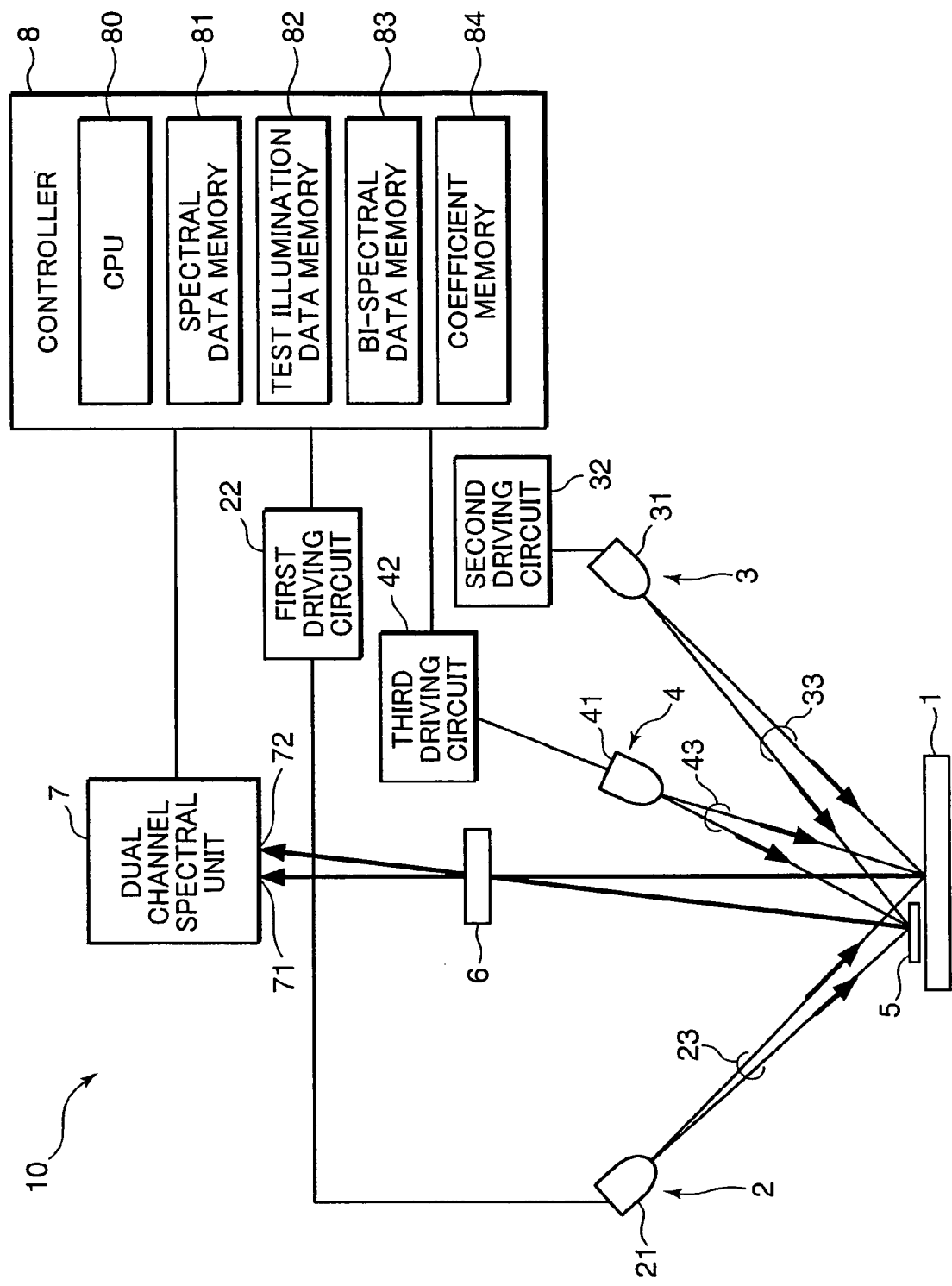
FIG. 1 is a diagram schematically showing an arrangement of an optical property measuring apparatus embodying the invention.

In the following, an embodiment of the invention is described referring to the drawings. Elements having like reference numerals throughout the drawings have like arrangements, and repeated description thereof is omitted herein.

FIG. 1 is a diagram schematically showing an arrangement of an optical property measuring apparatus 10 embodying the invention. Referring to FIG. 1, the optical property measuring apparatus 10 is an apparatus for measuring an optical property (whiteness or color) of a measurement sample 1, and includes a first illuminating unit 2, a second illuminating unit 3, a third illuminating unit 4, a reference plane 5, a receiving optics 6, a dual channel spectral unit 7, and a controller 8.

The measurement sample 1 is a sample to be measured, such as FWA treated paper, FWA treated fabric, or a printed sample on an FWA treated substrate. The measurement sample 1 is placed at a predetermined measurement position in the optical property measuring apparatus 10.

The first illuminating unit 2 is operable to illuminate the measurement sample 1, and serves as a light source. The first illuminating unit 2 is constituted of a white LED 21 for outputting a white light flux having a predetermined spectral distribution, and a first driving circuit 22 for driving the white LED 21 to turn on the white LED 21. Similarly to the first illuminating unit 2, the second illuminating unit 3 is operable to illuminate the measurement sample 1, and serves as a light source. The second illuminating unit 3 is constituted of a purple LED 31 for outputting a light flux in a purple region, and a second driving circuit 32 for driving the purple LED 31 to turn on the purple LED 31. Similarly to the first illuminating unit 2, the third illuminating unit 4 is operable to illuminate the measurement sample 1, and serves as a light source (UV light source). The third illuminating unit 4 is constituted of a UV LED 41 for outputting a light flux in a UV region, and a third driving circuit 42 for driving the UV LED 41 to turn on the UV LED 41.

The reference plane 5 is a white and diffusively reflecting member as a reference surface or a reflecting surface, and is disposed near a measuring area of the measurement sample 1. The receiving optics 6, as a light receiving system, has an optical lens or lenses. The receiving optics 6 is operable to receive radiation including fluoresced light from the measurement sample 1 illuminated by an illumination 23, 33, 43 to be emitted from the first, the second, the third illuminating unit 2, 3, 4; and a light component in a normal direction of reflecting light from the reference plane 5, excluding fluoresced light, and allows the received light flux to be incident toward the dual channel spectral unit 7 to be described later.

The dual channel spectral unit 7 is operable to perform spectral measurement of light incident from the receiving optics 6. The dual channel spectral unit 7 has a first incident slit 71 and a second incident slit 72. Radiation from the measurement sample 1 illuminated by the illumination 23, 33, 43 is incident onto the first incident slit 71. On the other hand, reflection from the reference plane 5 illuminated by the illumination 23, 33, 43 is incident onto the second incident slit 72. The dual channel spectral unit 7 is operable to perform spectral measurement of sample radiation incident onto the first incident slit 71 to output spectral distribution data on the sample radiation, as a first channel output; and perform spectral measurement of reference reflection (reference light) (in other words, the illumination 23, 33, 43 itself) incident onto the second incident slit 72 to output spectral distribution data on the illumination 23, 33, 43, as a second channel output. In this way, the dual channel spectral unit 7 functions as an analyzer for performing spectral measurement and outputting spectral measurement data.

The controller 8 includes an ROM (Read Only Memory) for storing control programs or the like, an RAM (Random Access Memory) for storing data on computation processing or control processing, and a CPU (Central Processing Unit) for reading the control programs or the like from the ROM for execution. The controller 8 controls overall operations of the optical property measuring apparatus 10. Specifically, the controller 8 functions as a processor, and controls driving on emission operations of the first illuminating unit 2, the second illuminating unit 3, and the third illuminating unit 4, and light receiving and spectral operations of the dual channel spectral unit 7. The controller 8 also executes various computation processing on calculation of a total spectral radiance factor of the measurement sample 1, selection of a bi-spectral luminescent radiance factor, and estimation of an effective bi-spectral luminescent radiance factor relative to the bi-spectral luminescent radiance factor of a printed sample, based on spectral information to be outputted from the dual channel spectral unit 7. The various computing functions of the controller 8 will be described later.

In use of the optical property measuring apparatus 10 having the above components, when the CPU 80 in the controller 8 controls the first driving circuit 22 to turn on the white LED 21, the white LED 21 illuminates the measurement sample 1 with the illumination (light flux) 23 at an incident angle of about 45° with respect to the normal to the measurement sample 1. Similarly, when the CPU 80 controls the second driving circuit 32 to turn on the purple LED 31, the purple LED 31 illuminates the measurement sample 1 with the illumination (light flux) 33 at an incident angle of about 45° with respect to the normal to the measurement sample 1. On the other hand, when the CPU 80 controls the third driving circuit 42 to turn on the UV LED 41, the UV LED 41 illuminates the measurement sample 1 with the illumination (light flux) 43 in a direction close to the normal than the incident angle 450 of the light flux 33. In other words, the UV LED 41 illuminates the measurement sample 1 with the illumination (light flux) 43 in a direction of an angle smaller than about 45° with respect to the normal to the measurement sample 1.

Figure 2:
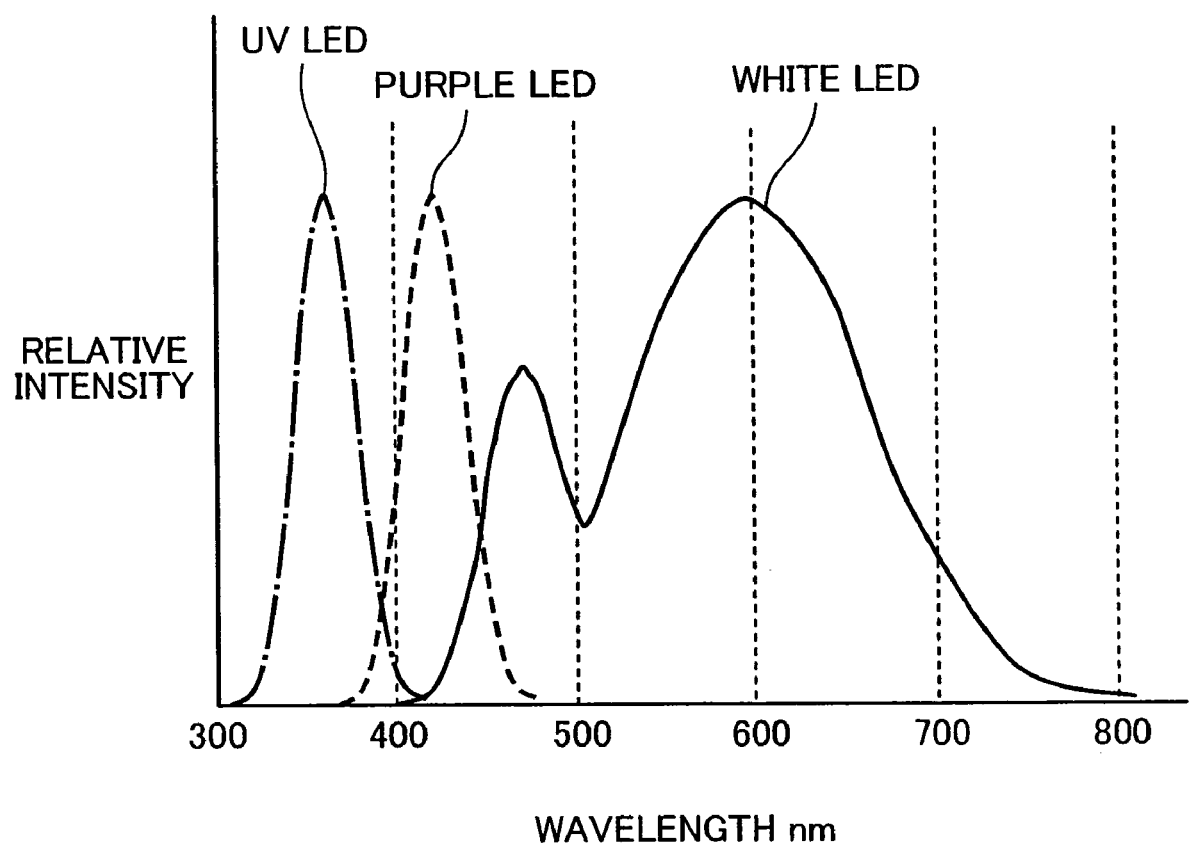
FIG. 2 is a graph showing spectral distributions of a white LED, a purple LED, and a UV LED.

FIG. 2 shows relative spectral distributions of light to be outputted from the white LED 21, the purple LED 31, and the UV LED 41. In FIG. 2, the horizontal axis indicates a wavelength (unit: nm), and the vertical axis indicates a relative intensity. The relative spectral distribution of the white LED 21 is indicated by the solid line, the relative spectral distribution of the purple LED 31 is indicated by the broken line, and the relative spectral distribution of the UV LED 41 is indicated by the one-dotted chain line.

In this embodiment, the first illuminating unit 2 and the second illuminating unit 3 function as a first illuminator. An illumination obtained by combining the illuminations 23 and 33 by simultaneously turning on the first illuminating unit 2 and the second illuminating unit 3 is defined as a first illumination I1. The first illuminating unit 2, the second illuminating unit 3, and the third illuminating unit 4 function as a second illuminator. An illumination obtained by combining the illuminations 23, 33, and 43 by simultaneously turning on the first illuminating unit 2, the second illuminating unit 3, and the third illuminating unit 4 is defined as a second illumination I2. Since both of the white LED 21 and the purple LED 31 are turned on for defining the first illumination I1 and the second illumination I2, the first illumination I1 and the second illumination I2 cover a visible region from 400 to 700 nm, as shown in FIG. 2, and correspond to the first illumination and the second illumination in D2, respectively. The second illumination I2 containing the illumination 43 from the UV LED 41 has a large excitation intensity with respect to a general fluorescent whitening agent, as compared with the first illumination I1 excluding the illumination 43 from the UV LED 41.

A light component in a substantially normal direction out of radiations from the measurement sample 1 illuminated by the first illumination I1 and the second illumination I2 is incident from the receiving optics 6 onto the first incident slit 71 of the dual channel spectral unit 7, and spectrally measured by the dual channel spectral unit 7. Then, spectral distributions Sx1($\lambda$) and Sx2($\lambda$) of the incident light component are outputted to the controller 8 as the first channel output. On the other hand, the reference plane 5 disposed near the measuring area of the measurement sample 1 is illuminated by the first illumination I1 and the second illumination I2 simultaneously with the surface of the measurement sample 1. Thereby, a light component in a substantially normal direction out of reflection from the reference plane 5 is incident from the receiving optics 6 onto the second incident slit 72 of the dual channel spectral unit 7, and spectrally measured by the dual channel spectral unit 7. Then, spectral distributions Mx1($\lambda$) and Mx2($\lambda$) of the incident light component are outputted to the controller 8 as the second channel output.

The center wavelength of the purple LED 31 in the second illuminating unit 3 is about 410 nm. The center wavelength of the UV LED 41 in the third illuminating unit 4 is about 375 nm. Thus, both of the center wavelengths of the purple LED 31 and the UV LED 41 lie in an excitation region of a general fluorescent whitening agent. In this embodiment, it is necessary to obtain a spectral distribution of the illuminations 23, 33, and 43 (second illumination I2) of a widest wavelength band. In view of this, the dual channel spectral unit 7 covers a wavelength region from about 360 nm to 700 nm, including a wavelength region of radiation from the UV LED 31. In other words, the dual channel spectral unit 7 is operable to perform spectral measurement in the target wavelength region.

The optical system of the optical property measuring apparatus 10 has 45/0 geometry (geometry for measuring a reflection characteristic: 45 degrees/0 degree) by combination (arrangement) of the first illuminating unit 2, the second illuminating unit 3, and the receiving optics 6 as described above. The aforementioned geometry is used to control specular reflection from the measurement sample 1. Specular reflection by the third illuminating unit 4 having no spectral distribution in the visible region does not affect colorimetry. Accordingly, the third illuminating unit 4 can be arranged at any position without constraints of the geometry.

In the following, details of the functional parts of the controller 8 are described. As shown in FIG. 1, the controller 8 includes the CPU 80, a spectral data memory 81, a test illumination data memory 82, a bi-spectral data memory 83, and a coefficient memory 84. The CPU 80 is a Central Processing Unit (CPU) for performing various computation processing such as computation on driving control of the first illuminating unit 2, the second illuminating unit 3, and the third illuminating unit 4, computation on driving control of the dual channel spectral unit 7, calculation of a total spectral radiance factor of the measurement sample 1, and computation on calibration of a relative spectral sensitivity.

The spectral data memory 81 is a circuit for storing spectral distribution data on illumination i.e. radiation from the measurement sample 1 and reflection from the reference plane 5 that has been spectrally measured by the dual channel spectral unit 7, and transmitted (outputted) from the dual channel spectral unit 7. The test illumination data memory 82 is a circuit for storing spectral distribution data on a test illumination given in advance. The bi-spectral data memory 83 is a circuit for storing data relating to typical bi-spectral luminescent radiance factors in advance.

The coefficient memory 84 is a circuit for storing coefficient data such as a conversion coefficient to be used in converting a spectral distribution of reflection (hereinafter, called as "reference reflection") from the reference plane 5 into a spectral distribution of illumination (hereinafter, called as "sample illumination") for illuminating the measurement sample 1; and a calibration coefficient to be used in obtaining a total spectral radiance factor of the measurement sample 1, based on spectral distributions of radiation (hereinafter, called as "sample radiation") from the measurement sample 1, and the reference reflection.

The controller 8 performs measurement control (computation) relating to the following steps, based on the spectral distribution data on radiation and illumination, the spectral distribution data on test illumination, the bi-spectral luminescent radiance factor data, and the coefficient data such as a conversion coefficient and a calibration coefficient, which are stored in the spectral data memory 81, the test illumination data memory 82, the bi-spectral data memory 83, and the coefficient memory 84, respectively.

Figure 3:
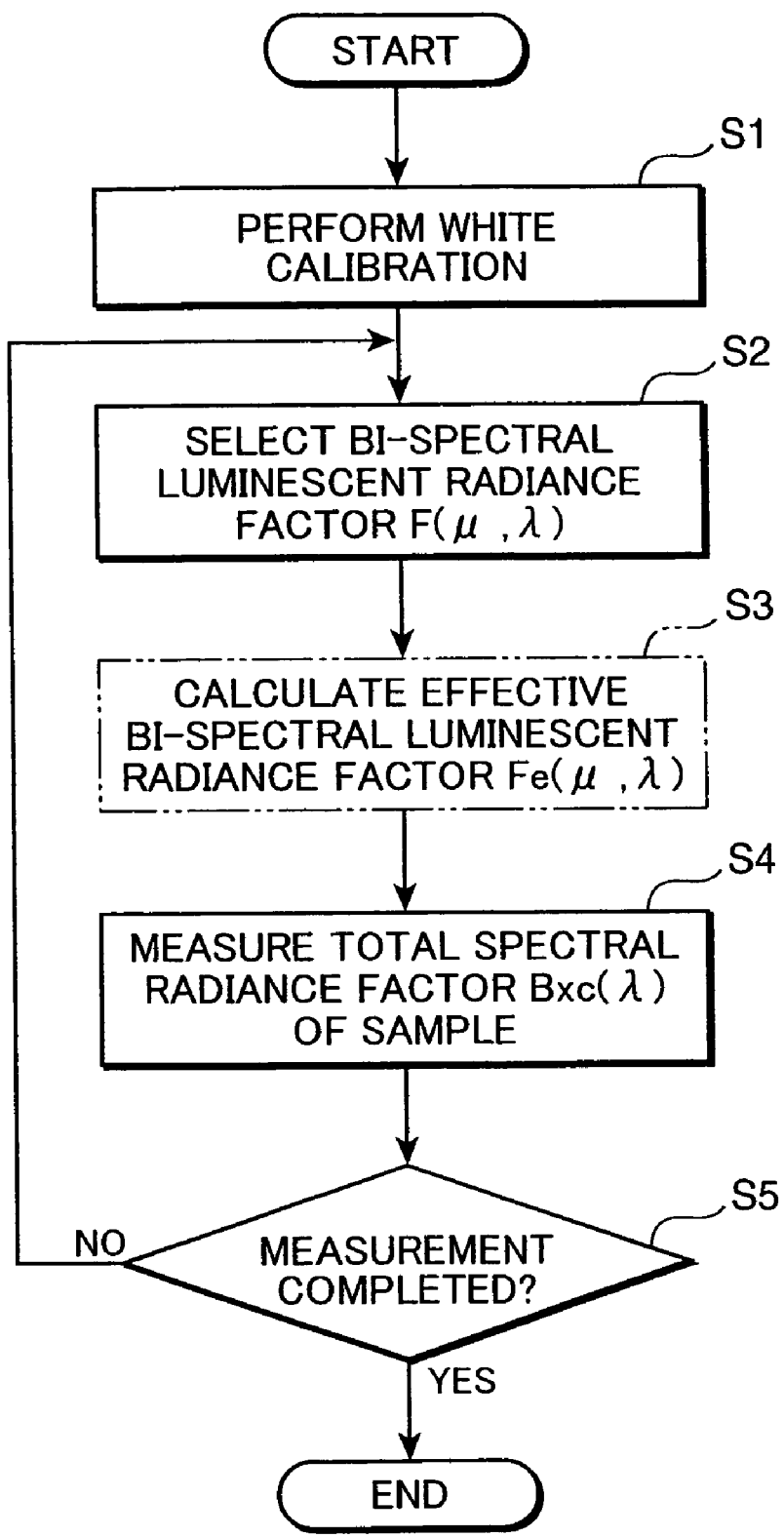
FIG. 3 is a flowchart showing the entirety of an operation of measuring a total spectral radiance factor of a fluorescent sample to be performed by the optical property measuring apparatus shown in FIG. 1.

FIG. 3 is a flowchart showing the entirety of an operation of measuring a total spectral radiance factor of a fluorescent sample to be performed by the optical property measuring apparatus shown in FIG. 1.

First, a total spectral radiance factor of the measurement sample 1 is measured. More specifically, four steps shown in FIG. 3 are executed. Prior to actual sample measurement, white calibration is performed (Step S1), wherein a calibration coefficient for use in converting spectral distributions of sample radiation and illumination into a reflectivity factor of the measurement sample 1 is obtained and stored in the coefficient memory 84. Then, a bi-spectral luminescent radiance factor relatively close to the bi-spectral luminescent radiance factor $F(\mu,\lambda)$ of the measurement sample 1 is selected from two typical bi-spectral luminescent radiance factors $Fc(\mu,\lambda)$ and $Fnc(\mu,\lambda)$ stored in the bi-spectral data memory 83 in advance (Step S2). In the case where the measurement sample 1 is a printed sample on an FWA treated substrate, an effective bi-spectral luminescent radiance factor relative to the bi-spectral luminescent radiance factor $F(\mu,\lambda)$ of the measurement sample 1, considering a transmittance of a printed ink, is estimated (Step S3). Then, a total spectral radiance factor $Bxc(\lambda)$ of the measurement sample 1 illuminated by a test illumination Is is calculated, based on the selected bi-spectral luminescent radiance factor $F(\mu,\lambda)$ or the estimated effective bi-spectral luminescent radiance factor $Fe(\mu,\lambda)$ (Step S4). In the case where multiple measurement samples 1 are measured, a judgment as to whether measurement is completed is made for all the measurement samples 1 (Step S5), and Steps S2 through S4 are repeated depending on the judgment result. The white calibration in Step S1, and the estimation of the effective bi-spectral luminescent radiance factor $Fe(\mu,\lambda)$ of a printed sample in Step S3 are described in detail in e.g. D2.

Figure 4:
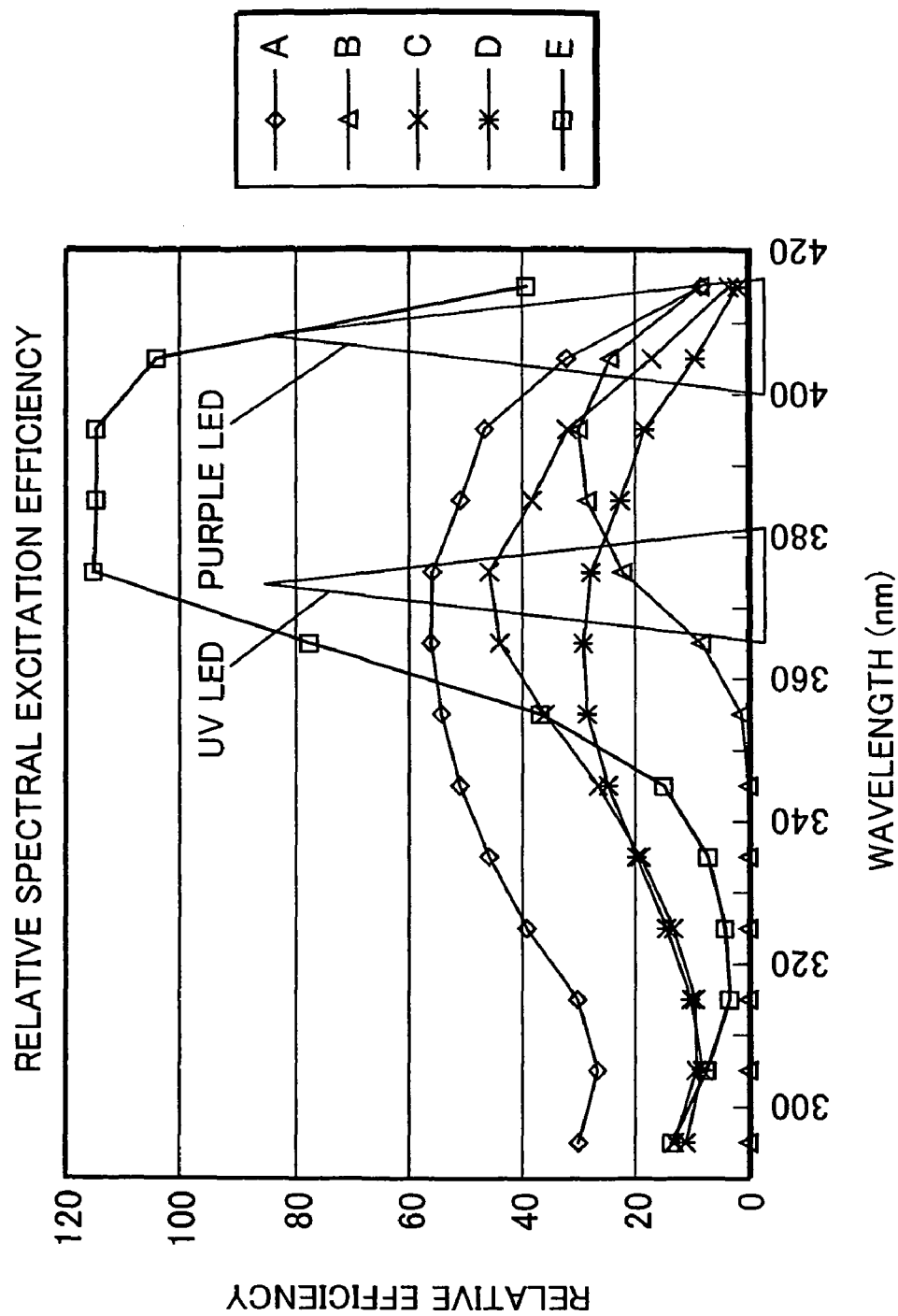
FIG. 4 is a graph showing spectral excitation efficiencies of FWA treated paper, as a representative example of the fluorescent sample, with respect to fluoresced light of 450 nm.

FIG. 4 is a graph showing spectral excitation efficiencies of FWA treated paper, as a representative example of a fluorescent sample, with respect to fluoresced light of 450 nm. In FIG. 4, the horizontal axis indicates a wavelength (unit: nm), and the vertical axis indicates a relative efficiency.

In the following, the operation of selecting a bi-spectral luminescent radiance factor in Step S2 is described. FIG. 4 shows spectral excitation efficiencies of multiple typical FWA treated paper with respect to fluoresced light of 450 nm (corresponding to a peak of fluorescent intensity), and spectral distributions of output light from the purple LED 31 and the UV LED 41. The spectral excitation efficiencies with respect to fluoresced light of 450 nm are extracted based on a bi-spectral luminescent radiance factor $F(\mu,\lambda)$ which is a spectral excitation efficiency at each fluorescent wavelength. As shown in FIG. 4, the bi-spectral excitation efficiencies of typical FWA treated paper are roughly classified into bi-spectral excitation efficiencies (indicated by the curves "B" and "E" in FIG. 4) of coated paper whose spectral excitation efficiency in a wavelength region of not longer than 360 nm is extremely low, because excitation illuminations are absorbed in a short wavelength region; and bi-spectral excitation efficiencies (indicated by the curves "A", "C", and "D") of plain paper whose spectral excitation efficiency is retained even in a wavelength region of not longer than 360 nm.

Let it be assumed that spectral distributions of sample radiation in a fluorescent region, which have been measured by illuminating a measurement sample 1 with a third illumination I3 (wavelength: 410 nm) from the purple LED 31 alone, and a fourth illumination I4 (wavelength: 375 nm) from the UV LED 41 alone are $Sx3(\lambda)$ and $Sx4(\lambda)$, respectively. Also, let it be assumed that spectral distributions of the third illumination I3 and the fourth illumination I4, which have been measured based on a simultaneously measured spectral distribution of reflection from the reference plane 5 are $I3(\mu)$ and $I4(\mu)$, respectively. Then, excitation efficiencies Ex3 and Ex4 of the measurement sample 1 illuminated by the third and the fourth illuminations I3 and I4 can be obtained by the following Equations (10) and (11), respectively.

$$Ex3 = \int Sx3(450) d\lambda \int I3(\mu) d\mu \quad (10)$$

$$Ex4 = \int Sx4(450) d\lambda \int I4(\mu) d\mu \quad (11)$$

The purple LED 31 and the UV LED 41 function as excitation illuminators, when operated alone.

A relative ratio Rex between the excitation efficiencies Ex3 and Ex4 expressed by the Equations (10) and (11) is expressed by the Equation (12).

$$Rex = Ex3/Ex4 \quad (12)$$

The excitation efficiency of plain paper is obviously smaller than the excitation efficiency of coated paper.

Accordingly, a judgment as to whether the measurement sample 1 is coated paper or plain paper can be made by discriminating the relative ratio Rex based on a predetermined threshold value. The CPU 80 is operable to perform the above discrimination and select a bi-spectral luminescent radiance factor corresponding to the type of the measurement sample 1 by storing the typical bi-spectral luminescent radiance factors $Fc(\mu,\lambda)$ and $Fnc(\mu,\lambda)$ of coated paper and plain paper, whereby an optical property of the measurement sample 1 can be measured with practically sufficient precision.

Figure 5:
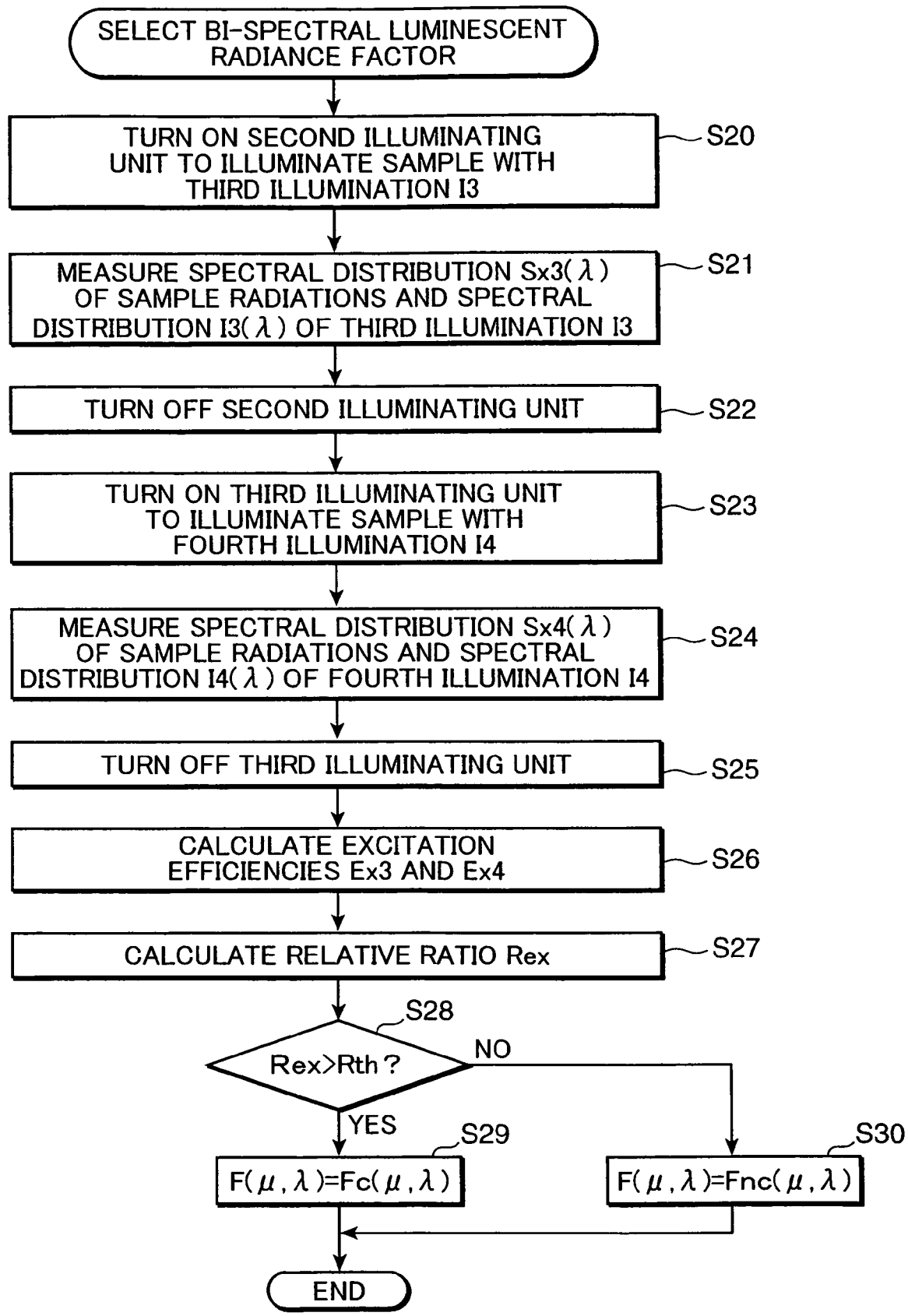
FIG. 5 is a flowchart showing an operation of selecting a bi-spectral luminescent radiance factor of a fluorescent sample in measuring the total spectral radiance factor.

FIG. 5 is a flowchart showing an operation of selecting the bi-spectral luminescent radiance factor $Fc(\mu,\lambda)$, $Fnc(\mu,\lambda)$ of a fluorescent sample (measurement sample 1), in measuring a total spectral radiance factor of the measurement sample 1.

Referring to FIG. 5, the CPU 80 in the controller 8 turns on only the second illuminating unit 3 (purple LED 31) to illuminate the measurement sample 1 placed at the measurement aperture by the illumination 33 (third illumination I3) (Step S20). Then, the dual channel spectral unit 7 measures a spectral distribution Sx3($\lambda$) of sample radiation by the illumination 33, measures a spectral distribution of reference reflection, acquires a conversion coefficient stored in the coefficient memory 84, using the spectral distribution of reference reflection, converts the spectral distribution Sx3($\lambda$) into a spectral distribution I3($\lambda$) of the third illumination I3 by the conversion coefficient, and stores the spectral distributions Sx3($\lambda$) and I3($\lambda$) into the spectral data memory 81 (Step S21). Then, the second illuminating unit 3 is turned off (Step S22).

Then, the CPU 80 turns on only the third illuminating unit 4 (UV LED 41) to illuminate the measurement sample 1 by the illumination 43 (fourth illumination I4) (Step S23). Then, similarly to Step S21, the dual channel spectral unit 7 measures a spectral distribution Sx4($\lambda$) of sample radiation by the illumination 43, measures a spectral distribution of reference reflection, acquires a conversion coefficient stored in the coefficient memory 84, using the spectral distribution of reference reflection, converts the spectral distribution Sx4($\lambda$) into a spectral distribution I4($\lambda$) of the fourth illumination I4 by the conversion coefficient, and stores the spectral distributions Sx4($\lambda$) and I4($\lambda$) into the spectral data memory 81 (Step S24). Then, the third illuminating unit 4 is turned off (Step S25).

Then, the CPU 80 calculates excitation efficiencies Ex3 and Ex4 by the third and the fourth illuminations I3 and I4 by the Equations (10) and (11), using the spectral distributions Sx3($\lambda$) and I3($\lambda$) stored in Step S21, and the spectral distributions Sx4($\lambda$) and I4($\lambda$) stored in Step S24 (Step S26). Then, the CPU 80 calculates a relative ratio Rex between the excitation efficiencies Ex3 and Ex4 by the Equation (12) (Step 27). Then, the relative ratio Rex is discriminated based on a predetermined threshold value Rth (Step S28). If it is judged that the relative ratio Rex is larger than the threshold value Rth (YES in Step S28), the bi-spectral luminescent radiance factor Fc($\mu$,$\lambda$) of coated paper is selected from the typical bi-spectral luminescent radiance factors Fc($\mu$,$\lambda$) and Fnc($\mu$,$\lambda$) of coated paper and plain paper stored in advance in the spectral data memory 83 (Step S29). If, on the other hand, it is judged that the relative ratio Rex is smaller than the threshold value Rth (NO in Step S28), the bi-spectral luminescent radiance factor Fnc($\mu$,$\lambda$) of plain paper is selected (Step S30). Thus, the routine is ended.

By performing the above operation, selection between the bi-spectral luminescent radiance factors Fc($\mu$,$\lambda$) and Fnc($\mu$,$\lambda$) of coated paper and plain paper is performed. When the selection is ended, the CPU 80 in the controller 8 calculates a total spectral radiance factor Bxc of the measurement sample 1 by a test illumination in the following manner.

Figure 6:
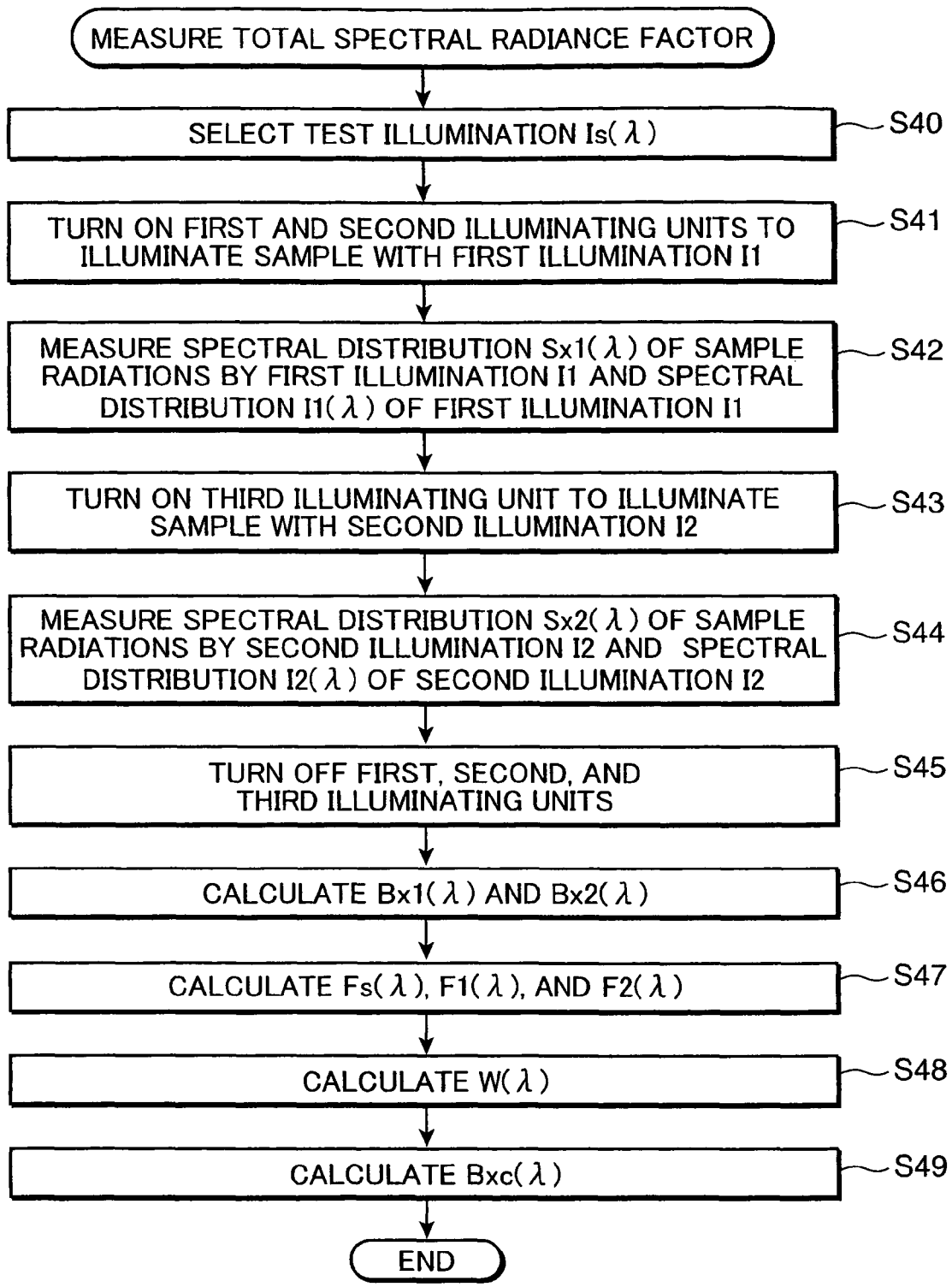
FIG. 6 is a flowchart showing the total spectral radiance factor measuring operation in detail.

FIG. 6 is a flowchart showing the operation of measuring a total spectral radiance factor in detail. FIG. 6 shows the operation in Step S4 in FIG. 3 in detail. First, prior to measurement, the CPU 80 selects a test illumination Is (Step S40). More specifically, the CPU 80 reads out spectral distribution data Is($\lambda$) (spectral distribution Is($\mu$)) of a test illumination Is to be selected from the test illumination data memory 82 (Step S40). Then, the CPU 80 turns on the first illuminating unit 2 (white LED 21) and the second illuminating unit 3 (purple LED 31) to illuminate the measurement sample 1 placed at the measurement aperture by the first illumination I1 (Step S41). Then, the CPU 80 controls the dual channel spectral unit 7 to measure a spectral distribution Sx1($\lambda$) of sample radiation by the first illumination I1, measure a spectral distribution of reference reflection, acquires a conversion coefficient stored in the coefficient memory 84 using the spectral distribution of reference reflection, converts the spectral distribution Sx1($\lambda$) into a spectral distribution I1($\lambda$) of the first illumination I1 by the conversion coefficient, and stores the spectral distributions Sx1($\lambda$) and I1($\lambda$) into the spectral data memory 81 (Step S42).

Then, the CPU 80 turns on the third illuminating unit 4 (UV LED 41), while keeping the on-state of the first illuminating unit 2 and the second illuminating unit 3 in Step S42, to illuminate the measurement sample 1 by the second illumination I2 to be defined by the first, the second, and the third illuminating units 2, 3, and 4 (Step S43). Then, similarly to Step S42, the dual channel spectral unit 7 measures a spectral distribution Sx2($\lambda$) of sample radiation by the second illumination I2, measures a spectral distribution of reference reflection, acquires a conversion coefficient stored in the coefficient memory 84 using the spectral distribution of reference reflection, converts the spectral distribution Sx2($\lambda$) into a spectral distribution I2($\lambda$) of the second illumination I1 by the conversion coefficient, and stores the spectral distributions Sx2($\lambda$) and I2($\lambda$) into the spectral data memory 81 (Step S44). Thereafter, the CPU 80 turns off the first, the second, and the third illuminating units 2, 3, and 4 (Step S45).

Then, the CPU 80 calculates total spectral radiance factors Bx1($\lambda$) and Bx2($\lambda$) by the first and the second illuminations I1 and I2 by the Equations (13) and (14), using a calibration coefficient K($\lambda$) stored in the coefficient memory 84, based on the spectral distributions Sx1($\lambda$) and I1($\lambda$) stored in Step S42 and the spectral distributions Sx2($\lambda$) and I2($\lambda$) stored in Step S44 (Step S46).

$$Bx1(\lambda)=K(\lambda) \cdot Sx1(\lambda)/I1(\lambda) \qquad (13)$$

$$Bx2(\lambda)=K(\lambda) \cdot Sx2(\lambda)/I2(\lambda) \qquad (14)$$

Then, the CPU 80 calculates a fluorescent spectral radiance factor F1($\lambda$) by the first illumination I1, a fluorescent spectral radiance factor F2($\lambda$) by the second illumination I2, and a fluorescent spectral radiance factor Fs($\lambda$) by the test illumination Is by the Equations (5), (6), and (7), respectively, based on the spectral distribution data Is($\mu$) read out in Step S40; the spectral distribution I1($\lambda$) stored in Step S42 and the spectral distribution I2($\lambda$) stored in Step S44; and the bi-spectral luminescent radiance factor F($\mu$,$\lambda$) selected in Step S2, or the effective bi-spectral luminescent radiance factor Fe($\mu$,$\lambda$) estimated in Step S3 using the selected bi-spectral luminescent radiance factor F($\mu$,$\lambda$) (Step S47).

Then, the CPU 80 obtains a weight W($\lambda$) by solving the Equation (8) at each wavelength, based on the calculated fluorescent spectral radiance factors F1($\lambda$), F2($\lambda$), and Fs($\lambda$) (Step S48). Then, the CPU 80 calculates total spectral radiance factor Bxc($\lambda$) close to the total spectral radiance factor of the measurement sample 1 illuminated by the test illumination Is by the Equation (9), based on the total spectral radiance factors Bx1($\lambda$) and Bx2($\lambda$) calculated in Step S46, and the weight W($\lambda$) calculated in Step S48 (Step S49).

By performing the above operation, in the case where an optical property (total spectral radiance factor Bxc($\lambda$)) of the measurement sample 1 such as an FWA treated sample or a printed sample on an FWA treated substrate illuminated by the test illumination Is is obtained, using the first illumination I1 and the second illumination I2 whose relative spectral distributions are different from each other, the typical bi-spectral luminescent radiance factors Fc($\mu$,$\lambda$) and Fnc($\mu$,$\lambda$) of coated paper and plain paper, as typical examples of FWA treated paper, are stored in advance in the bi-spectral data memory 83; the measurement sample 1 is illuminated by multiple excitation illuminations (third and the fourth illuminations I3 and I4) whose spectral distributions are different from each other; the excitation efficiencies Ex3 and Ex4 are measured; a bi-spectral luminescent radiance factor relatively close to the bi-spectral characteristics of the measurement sample 1 is automatically selected from the bi-spectral luminescent radiance factors Fc(μ,λ) and Fnc(μ,λ) stored in advance, based on the relative ratio Rex between the excitation efficiencies Ex3 and Ex4; and the total spectral radiance factor Bxc(λ) is obtained, using the selected bi-spectral luminescent radiance factor.

Accordingly, the optical property measuring apparatus 10 of the embodiment enables to eliminate the need of a fluorescent standard or a cumbersome calibration, and obtain an optical property (total spectral radiance factor Bxc(λ)) of the measurement sample 1 easily and with high precision, without imparting a load to a user in selecting a bi-spectral luminescent radiance factor of the measurement sample 1.

The bi-spectral luminescent radiance factor to be selected is e.g. the bi-spectral luminescent radiance factor Fc(μ,λ), Fnc(μ,λ) of coated paper, plain paper. The operation of selecting the bi-spectral luminescent radiance factor Fc(μ,λ), Fnc(μ,λ) of coated paper, plain paper comprises: steps (Steps S20 and S22; Steps S23 and S25) of illuminating the measurement sample 1 and the reference plane 5 by the third illumination I3 and the fourth illumination I4 having respective excitation regions and spectral distributions different from each other; steps (Steps S21 and S24) of measuring spectral distributions of sample radiation from the measurement sample 1 and reference reflection from the reference plane 5 illuminated by the third illumination I3, and measuring spectral distributions of sample radiation from the measurement sample 1 and reference reflection from the reference plane 5 illuminated by the fourth illumination I4; a step (Step S26) of obtaining excitation efficiencies Ex3 and Ex4 by the third illumination I3 and the fourth illumination I4, based on the spectral distributions Sx3(λ) and Sx4(λ) of sample radiations from the measurement sample 1, and the spectral distributions I3(λ) and I4(λ) of the third and the fourth illuminations I3 and I4 derived from reference reflection from the reference plane 5; a step (Step S27) of obtaining a relative ratio Rex between the excitation efficiencies Ex3 and Ex4 by the third and the fourth illuminations I3 and I4; and steps (Steps S28 through S30) of discriminating the relative ratio Rex based on the predetermined threshold value Rth, and selecting the bi-spectral luminescent radiance factor Fc(μ,λ) or Fnc(μ,λ) relatively close to the bi-spectral luminescent radiance factor of the measurement sample 1. Accordingly, the optical property measuring apparatus 10 of the embodiment is advantageous in measuring a bi-spectral luminescent radiance factor with practically sufficient precision, while avoiding erroneous selection.

In the case where the measurement sample 1 is a printed sample on FWA treated paper, in Step S2 of selecting the bi-spectral luminescent radiance factor F(μ,λ) excitation efficiencies of non-printed FWA treated paper illuminated by the third and the fourth illuminations I3 and I4 are obtained, and similarly to the above, a bi-spectral luminescent radiance factor Fc(μ,λ), Fnc(μ,λ) relatively close to the bi-spectral luminescent radiance factor of FWA treated paper is selected, and an effective bi-spectral luminescent radiance factor Fe(μ, λ) of the measurement sample 1 is estimated, based on the selected bi-spectral luminescent radiance factor, and an effective transmittance of an ink printed on the FWA treated paper (Step S3). Accordingly, the optical property measuring apparatus 10 of the embodiment is advantageous in measuring a total spectral radiance factor Bxc(λ) of a printed sample on FWA treated paper with practically sufficient precision, without imparting a load to a user.

The LED 31 and the LED 41 as multiple excitation illuminators are monochromatic light sources having center wavelengths different from each other in an excitation region. Accordingly, the optical property measuring apparatus 10 of the embodiment is advantageous in easily selecting the bi-spectral luminescent radiance factor Fc(μ,λ) or Fnc(μ,λ) by properly selecting the center wavelength.

Since the LED 31 and the LED 41 serve as the multiple excitation illuminators, the optical property measuring apparatus 10 of the embodiment is advantageous in producing a monochromatic excitation illuminator having sufficient spectral intensity and stability easily and with a low cost.

The LED 31 and the LED 41 are respectively the purple LED 31 and the UV LED 41. The first illumination I1 and the second illumination I2 are obtained by different combinations of output light from the purple LED 31, the UV LED 41, and the white LED 21. Accordingly, the optical property measuring apparatus 10 of the embodiment is advantageous in producing two excitation illuminators having sufficient spectral intensity and stability, and two illuminators easily and with a low cost.

In the foregoing embodiment, the optical property measuring apparatus 10 is configured in such a manner that the first illuminating unit 2 and the second illuminating unit 3 serving as the first illumination I1 are simultaneously turned on; and the first illuminating unit 2, the second illuminating unit 3, and the third illuminating unit 4 serving as the second illumination I2 are simultaneously turned on.

Alternatively, the optical property measuring apparatus 10 may be configured in such a manner that the first illuminating unit 2, the second illuminating unit 3, and the third illuminating unit 4 are individually turned on to obtain spectral distributions I5(λ), I3(λ), and I4(λ) of illuminations I5, I3, and I4 (the illumination by the white LED 21 alone is defined as the fifth illumination I5), and spectral distributions Sx5(λ), Sx3(λ), and Sx4(λ) of sample radiations by the fifth illumination I5, the third illumination I3, and the fourth illumination I4, in the similar manner as described above; and the aforementioned spectral distributions are numerically combined, whereby a spectral distribution I1(λ) of a first illumination I1, a spectral distribution I2(λ) of a second illumination I2, a spectral distribution Sx1(λ) of sample radiation by the first illumination I1, and a spectral distribution Sx2(λ) of sample radiation by the second illumination I2 are obtained, as expressed by the Equations (15) through (18).

$$I1(\lambda)=I5(\lambda)+I3(\lambda) \tag{15}$$

$$I2(\lambda)=I5(\lambda)+I3(\lambda)+I4(\lambda) \tag{16}$$

$$Sx1(\lambda)=Sx5(\lambda)+Sx3(\lambda) \tag{17}$$

$$Sx2(\lambda)=Sx5(\lambda)+Sx3(\lambda)+Sx4(\lambda) \tag{18}$$

Figure 7:
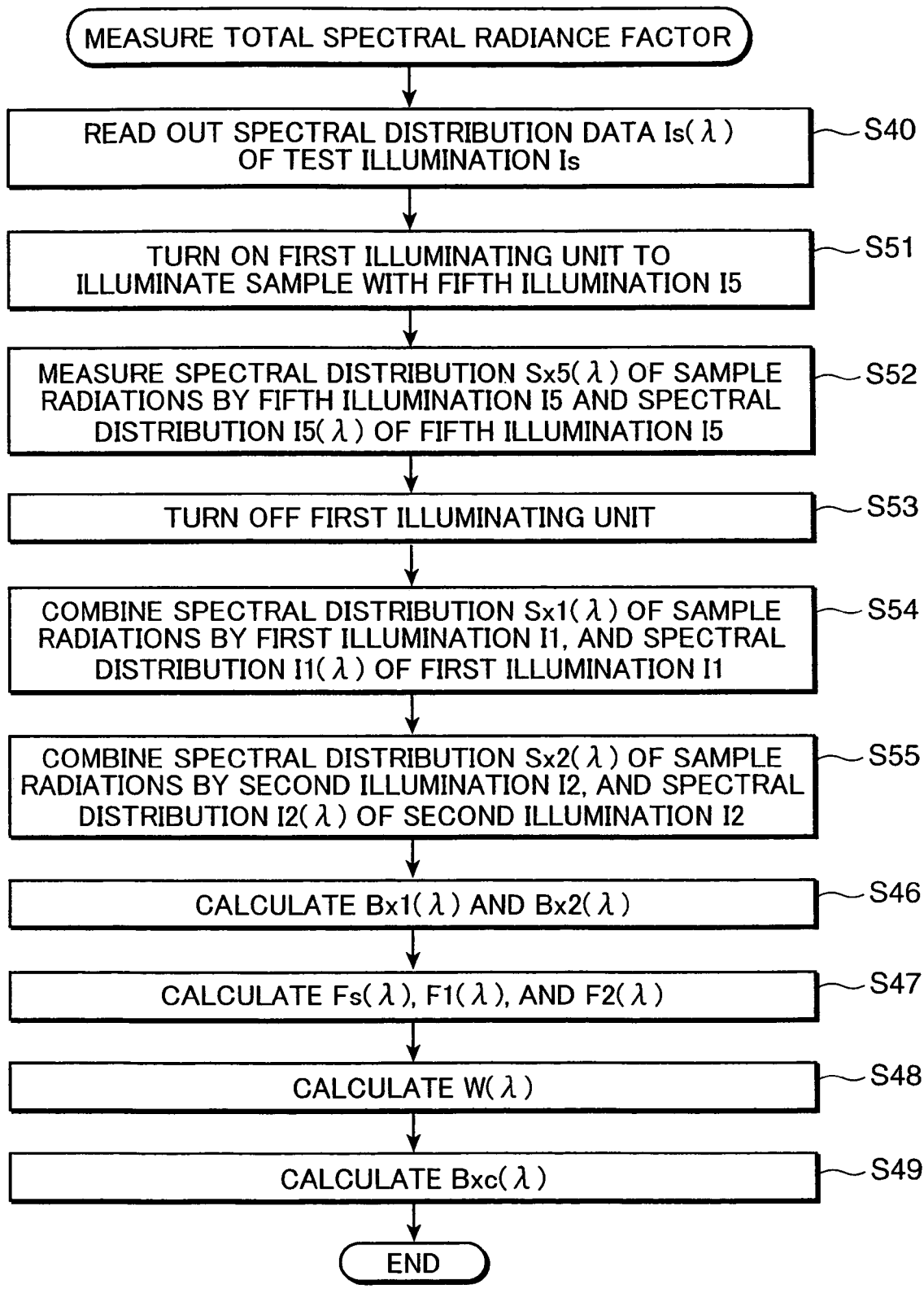
FIG. 7 is a flowchart showing a modification of the total spectral radiance factor measuring operation in detail.
Figure 8:
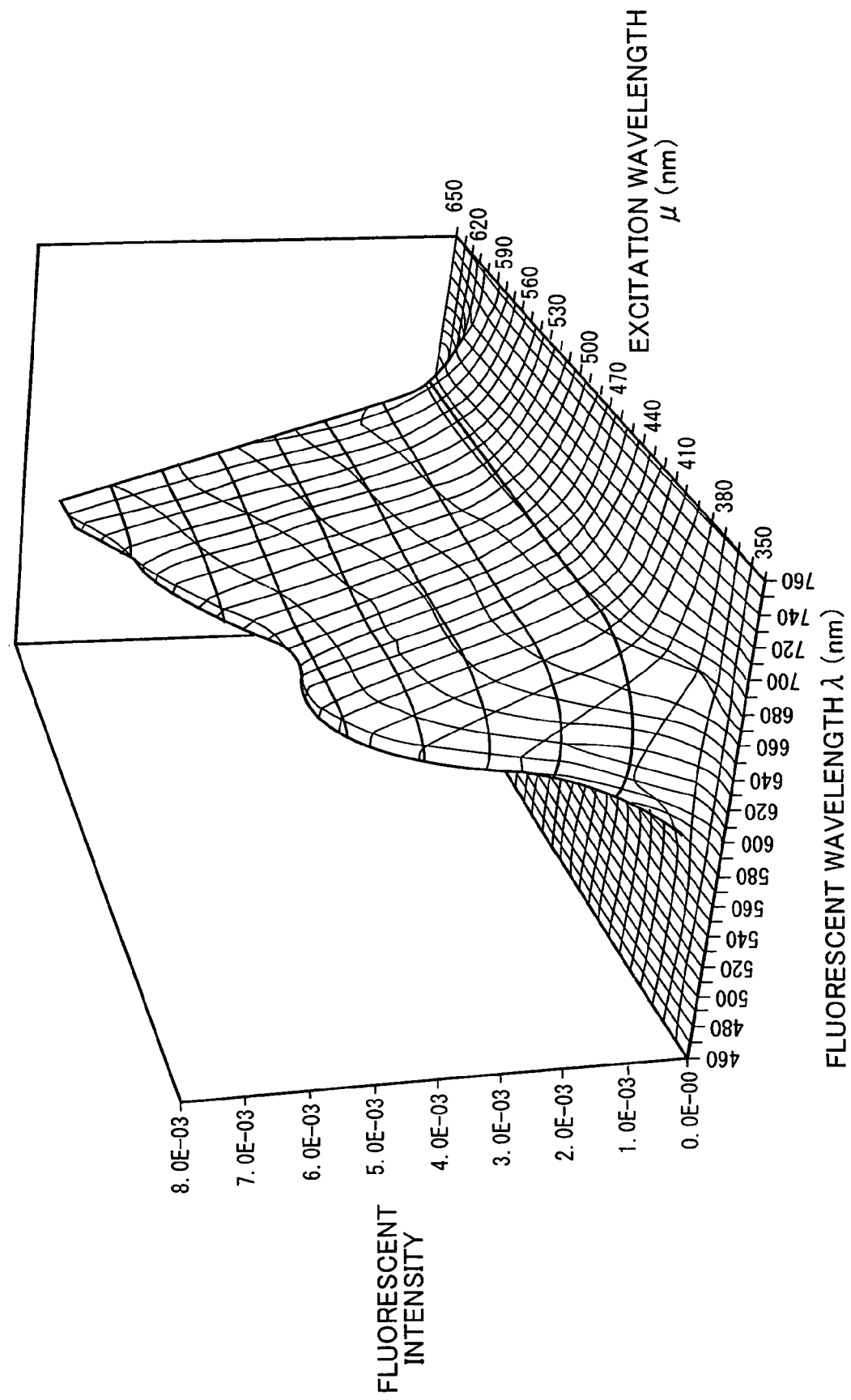
FIG. 8 is a graph showing matrix data on an intensity of a bi-spectral luminescent radiance factor.
Figure 9:
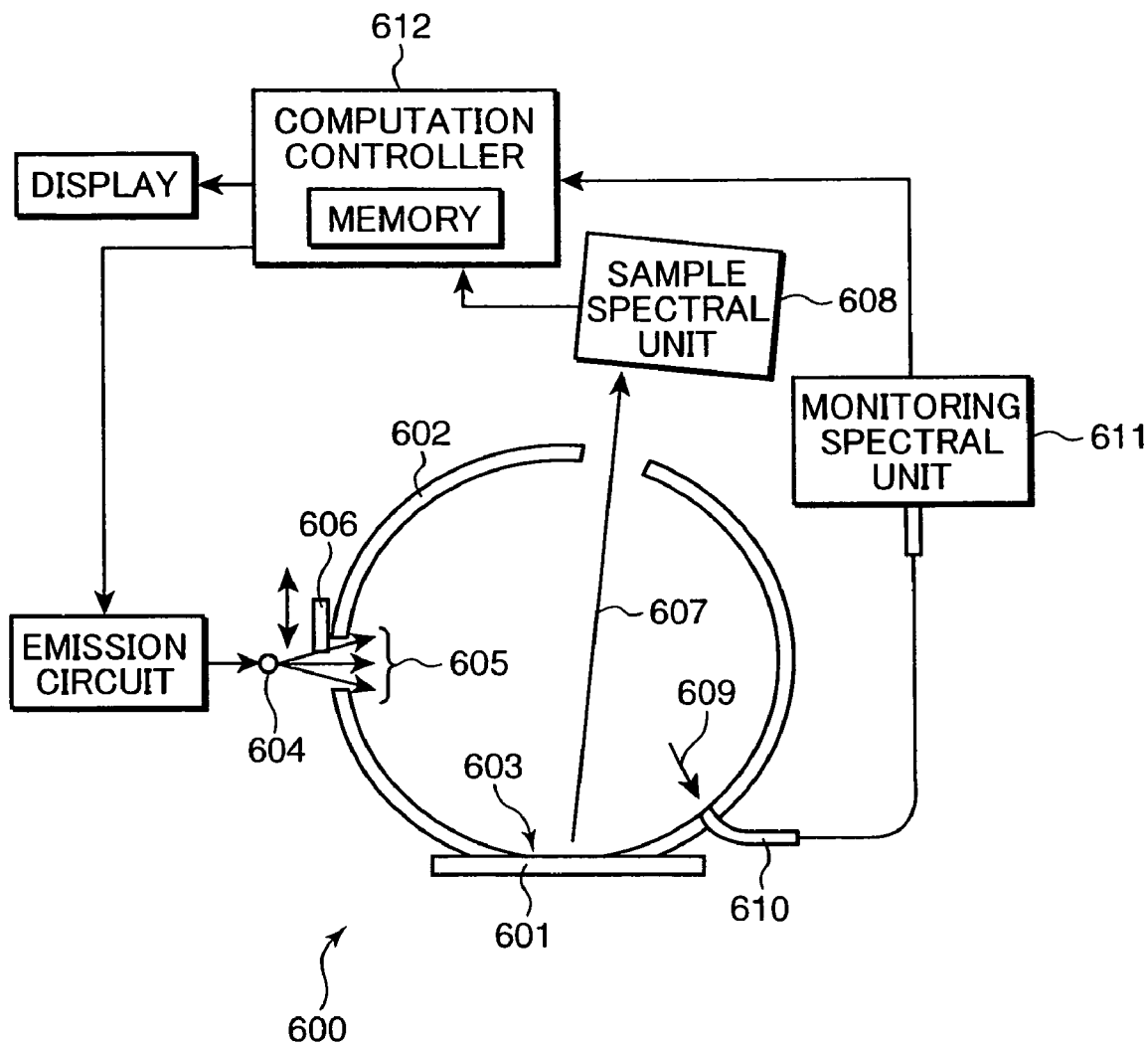
FIG. 9 is a diagram schematically showing an arrangement of a conventional optical property measuring apparatus.
Figure 10:
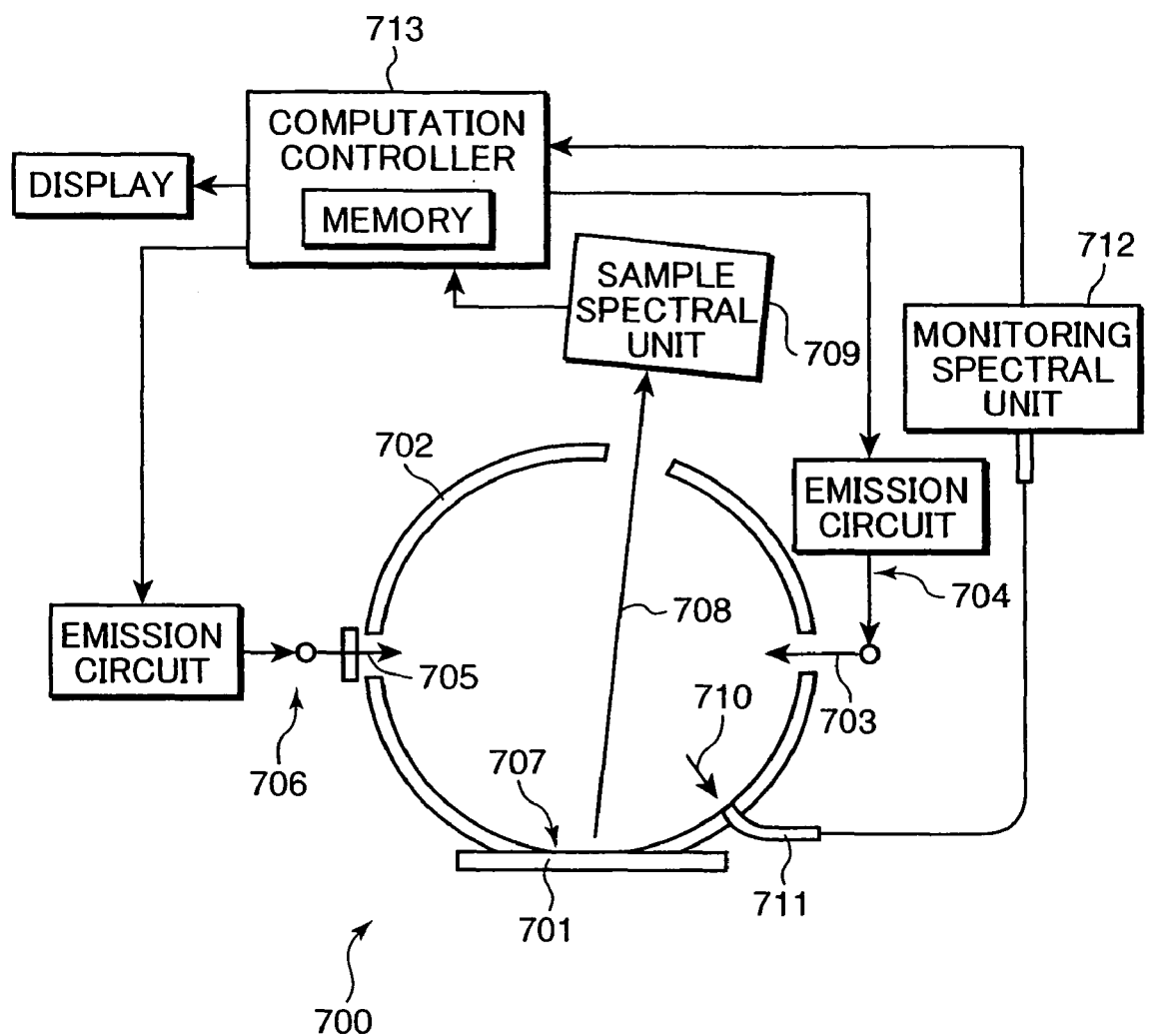
FIG. 10 is a diagram schematically showing an arrangement of another conventional optical property measuring apparatus.

FIG. 7 is a flowchart showing Step S4 in FIG. 3 in detail. Specifically, FIG. 7 is a flowchart showing a modification of the operation of measuring a total spectral radiance factor in detail. Similarly to FIG. 6, prior to measurement, the CPU 80 selects a test illumination Is (Step S40). Then, the CPU 80 turns on only the first illuminating unit 2 (white LED 21) as described above to illuminate the measurement sample 1 placed at the measurement aperture by the fifth illumination I5 (Step S51). Then, the CPU 80 controls the dual channel spectral unit 7 to measure a spectral distribution Sx5(λ) of sample radiation by the fifth illumination I5, measure a spectral distribution of reference reflections, acquire a conversion coefficient stored in the coefficient memory 84 using the spectral distribution of reference reflection, convert the spectral distribution Sx5($\lambda$) into a spectral distribution I5($\lambda$) of the fifth illumination I5 by the conversion coefficient, and store the spectral distributions Sx5($\lambda$) and I5($\lambda$) into the spectral data memory 81 (Step S52).

Then, the CPU 80 turns off the first illuminating unit 2 (white LED 21) (Step S53). Thereafter, the CPU 80 calculates spectral distributions I1($\lambda$) and Sx1($\lambda$) using the Equations (15) and (17), and spectral distributions I2($\lambda$) and Sx2($\lambda$) using the Equations (16) and (18), based on the spectral distributions I5($\lambda$) and Sx5($\lambda$), and the spectral distributions I3($\lambda$) and Sx3($\lambda$) obtained in Step S21, and the spectral distributions I4($\lambda$) and Sx4($\lambda$) obtained in Step S24 (Steps S54 and S55). Thereafter, the CPU 80 performs Steps S46 through S49 shown in FIG. 6 in the similar manner as described above.

The specification discloses the aforementioned arrangements. The following is a summary of the primary arrangements of the embodiment.

A method for measuring an optical property of a fluorescent sample according to an aspect of the invention includes: a step of storing multiple bi-spectral characteristics in advance; a step of measuring excitation efficiencies of the fluorescent sample by multiple excitation illuminations whose spectral distributions are different from each other in an excitation region of the fluorescent sample; a step of selecting bi-spectral characteristics relatively close to bi-spectral characteristics of the fluorescent sample out of the stored multiple bi-spectral characteristics based on ratios between the measured excitation efficiencies; and a step of obtaining the optical property of the fluorescent sample based on the selected bi-spectral characteristics.

The above arrangement enables to obtain an optical property of a fluorescent sample easily and with high precision, without imparting a load to a user in selecting a bi-spectral luminescent radiance factor of the fluorescent sample.

Preferably, the step of measuring excitation efficiencies of the fluorescent sample may include: illuminating the fluorescent sample by the multiple excitation illuminations; measuring spectral distributions of the multiple excitation illuminations, and radiations from the fluorescent sample illuminated by the excitation illuminations; and obtaining the excitation efficiencies of the fluorescent sample illuminated by the multiple excitation illuminations based on the measured spectral distributions of the excitation illuminations and the radiations. The step of selecting bi-spectral characteristics may include: calculating the ratios between the excitation efficiencies by the multiple excitation illuminations; discriminating the calculated ratios based on predetermined threshold values; and selecting bi-spectral characteristics relatively close to the bi-spectral characteristics of the fluorescent sample out of the stored multiple bi-spectral characteristics based on the discrimination results.

The above arrangement enables to measure bi-spectral characteristics with practically sufficient precision, while avoiding erroneous selection.

Preferably, the step of obtaining the optical property of the fluorescent sample may include: illuminating the fluorescent sample by a first illumination and a second illumination whose spectral distributions are different from each other; measuring spectral distributions of the first illumination and the second illumination, and radiations from the fluorescent sample illuminated by the first illumination and the second illumination; obtaining a first total spectral radiance factor and a second total spectral radiance factor of the fluorescent sample illuminated by the first illumination and the second illumination, respectively, based on the measured spectral distributions; calculating a first spectral fluorescent characteristic, a second spectral fluorescent characteristic, and a target spectral fluorescent characteristic of the fluorescent sample illuminated by the first illumination, the second illumination, and a predetermined test illumination given in advance, respectively, based on the selected bi-spectral characteristics, the measured spectral distributions of the first illumination and the second illumination, and a spectral distribution of the test illumination, determining a first weighting factor and a second weighting factor at each wavelength so that a linear combination of the first spectral fluorescent characteristic weighted by the first weighting factor, and the second spectral fluorescent characteristic weighted by the second weighting factor match with the target spectral fluorescent characteristic, and calculating a total spectral radiance factor of the fluorescent sample illuminated by the test illumination by linearly combining the first total spectral radiance factor weighted by the first determined weighting factor, and the second total spectral radiance factor weighted by the second determined weighting factor.

A method for measuring an optical property of a printed sample on paper treated by a fluorescent whitening agent according to another aspect of the invention includes: a step of selecting bi-spectral characteristics relatively close to bi-spectral characteristics of the paper treated by the fluorescent whitening agent according to any one of the aforementioned methods; a step of estimating effective bi-spectral characteristics of the printed sample based on the selected bi-spectral characteristics, and an effective spectral transmittance of an ink of the printed sample; and a step of obtaining the optical property of the printed sample based on the estimated effective bi-spectral characteristics.

The above arrangement enables to measure an optical property of a printed sample obtained by printing an ink on FWA treated paper easily and with practically sufficient precision, without imparting a load to a user.

An apparatus for measuring an optical property of a fluorescent sample according to another aspect of the invention includes: excitation illuminators for illuminating the fluorescent sample by multiple excitation illuminations whose spectral distributions are different from each other in an excitation region of the fluorescent sample; an analyzer for measuring spectral distributions of the excitation illuminations, and radiations from the fluorescent sample illuminated by the excitation illuminations; and a processor for controlling the excitation illuminators and the analyzer, and for processing the spectral distributions measured by the analyzer, wherein the processor is operable to illuminate the fluorescent sample by each of the excitation illuminations, measure a spectral distribution of each of the excitation illuminations, and the radiations from the fluorescent sample illuminated by the excitation illuminations, calculate an excitation efficiency of the fluorescent sample illuminated by each of the excitation illuminations based on the measured spectral distributions, calculate ratios between the calculated excitation efficiencies, discriminate the calculated ratios based on predetermined threshold values, select bi-spectral characteristics relatively close to bi-spectral characteristics of the fluorescent sample out of stored multiple bi-spectral characteristics based on the discrimination results, and obtain the optical property of the fluorescent sample based on the selected bi-spectral characteristics.

The above arrangement enables to obtain an optical property of a fluorescent sample easily and with high precision, without imparting a load to a user in selecting a bi-spectral luminescent radiance factor of the fluorescent sample. The above arrangement also enables to measure bi-spectral characteristics of a fluorescent sample with practically sufficient precision, while avoiding erroneous selection.

Preferably, the apparatus for measuring an optical property of a fluorescent sample may further include a first illuminator and a second illuminator to be controlled by the processor, and for illuminating the fluorescent sample by a first illumination and a second illumination whose spectral distributions are different from each other, wherein the processor is further operable to illuminate the fluorescent sample by each of the first illumination and the second illumination, measure the spectral distributions of the first illumination and the second illumination, and radiations from the fluorescent sample illuminated by the first illumination and the second illumination, and obtain the optical property of the fluorescent sample, based on a spectral distribution of a predetermined test illumination given in advance, and the selected bi-spectral characteristics.

Preferably, for estimating a total spectral radiance factor of the fluorescent sample illuminated by the test illumination, the processor may be operable to calculate a first total spectral radiance factor and a second total spectral radiance factor of the fluorescent sample illuminated by the first illumination and the second illumination, respectively, based on the measured spectral distributions of the first illumination, the second illumination, and the radiations from the fluorescent sample illuminated by the first illumination and the second illumination, calculate a first spectral fluorescent characteristic, a second spectral fluorescent characteristic, and a target spectral fluorescent characteristic of the fluorescent sample illuminated by the first illumination, the second illumination, and the test illumination, respectively, based on the selected bi-spectral characteristics, the measured spectral distributions of the first illumination and the second illumination, and the spectral distribution of the test illumination, determine a first weighting factor and a second weighting factor at each wavelength so that a linear combination of the first spectral fluorescent characteristic weighted by the first weighting factor, and the second spectral fluorescent characteristic weighted by the second weighting factor match with the target spectral fluorescent characteristic, and calculate a total spectral radiance factor of the fluorescent sample illuminated by the test illumination by linearly combining the first total spectral radiance factor weighted by the first determined weighting factor, and the second total spectral radiance factor weighted by the second determined weighting factor.

Preferably, the multiple excitation illuminators may be multiple monochromatic light sources whose center wavelengths are different from each other in the excitation region of the fluorescent sample. This arrangement enables to easily select bi-spectral characteristics of a fluorescent sample by properly selecting the center wavelength.

Preferably, the multiple excitation illuminators may be two kinds of LEDs. This arrangement enables to obtain monochromatic excitation illuminators having sufficient spectral intensity and stability easily and with a low cost.

Preferably, the two kinds of LEDs may be a purple LED and a UV LED, and the first illumination and the second illumination may be different combinations of output light from the purple LED and the UV LED as the excitation illuminators, and a white LED. This arrangement enables to obtain two excitation illuminators having sufficient spectral intensity and stability, and two illuminators easily and with a low cost.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. A method for measuring an optical property of a fluorescent sample, the method comprising:
   storing multiple bi-spectral characteristics in advance;
   measuring excitation efficiencies of a fluorescent sample by multiple excitation illuminations whose spectral distributions are different from each other in an excitation region of the fluorescent sample, wherein the measuring excitation efficiencies comprises:
      illuminating the fluorescent sample by the multiple excitation illuminations;
      measuring spectral distributions of the multiple excitation illuminations, and radiations from the fluorescent sample illuminated by the excitation illuminations; and
      obtaining the excitation efficiencies of the fluorescent sample illuminated by the multiple excitation illuminations based on the measured spectral distributions of the excitation illuminations and the radiations:
   selecting bi-spectral characteristics out of the stored multiple bi-spectral characteristics based on ratios between the measured excitation efficiencies, wherein the selecting bi-spectral characteristics comprises:
      calculating the ratios between the excitation efficiencies by the multiple excitation illuminations;
      discriminating the calculated ratios based on predetermined threshold values; and
      selecting bi-spectral characteristics out of the stored multiple bi-spectral characteristics based on the discrimination results; and
   obtaining an optical property of the fluorescent sample based on the selected bi-spectral characteristics.

2. The method for measuring an optical property of a fluorescent sample according to claim 1, wherein the obtaining the optical property of the fluorescent sample comprises:
   illuminating the fluorescent sample by a first illumination and a second illumination whose spectral distributions are different from each other;
   measuring spectral distributions of the first illumination and the second illumination, and radiations from the fluorescent sample illuminated by the first illumination and the second illumination;
   obtaining a first total spectral radiance factor and a second total spectral radiance factor of the fluorescent sample illuminated by the first illumination and the second illumination, respectively, based on the measured spectral distributions; calculating a first spectral fluorescent characteristic, a second spectral fluorescent characteristic, and a target spectral fluorescent characteristic of the fluorescent sample illuminated by the first illumination, the second illumination, and a predetermined test illumination given in advance, respectively, based on the selected bi-spectral characteristics, the measured spectral distributions of the first illumination and the second illumination, and a spectral distribution of the test illumination:
   determining a first weighting factor and a second weighting factor at each fluorescent wavelength so that a linear combination of the first spectral fluorescent characteristic weighted by the first weighting factor, and the second spectral fluorescent characteristic weighted by the second weighting factor match with the target spectral fluorescent characteristic; and calculating a total spectral radiance factor of the fluorescent sample illuminated by the test illumination by linearly combining the first total spectral radiance factor weighted by the first determined weighting factor, and the second total spectral radiance factor weighted by the second determined weighting factor.

3. A method for measuring an optical property of a printed sample on paper treated by a fluorescent whitening agent, the method comprising:
storing multiple bi-spectral characteristics in advance;
measuring excitation efficiencies of a fluorescent sample by multiple excitation illuminations whose spectral distributions are different from each other in an excitation region of the fluorescent sample, wherein the measuring excitation efficiencies comprises:
illuminating the fluorescent sample by the multiple excitation illuminations;
measuring spectral distributions of the multiple excitation illuminations, and radiations from the fluorescent sample illuminated by the excitation illuminations; and
obtaining the excitation efficiencies of the fluorescent sample illuminated by the multiple excitation illuminations based on the measured spectral distributions of the excitation illuminations and the radiations:
selecting bi-spectral characteristics out of stored multiple bi-spectral characteristics based on ratios between the measured excitation efficiencies, wherein the selecting bi-spectral characteristics comprises:
calculating the ratios between the excitation efficiencies by the multiple excitation illuminations;
discriminating the calculated ratios based on predetermined threshold values; and
selecting bi-spectral characteristics-out of the stored multiple bi-spectral characteristics based on the discrimination results; and
estimating effective bi-spectral characteristics of a printed sample on paper treated by a fluorescent whitening agent based on the selected bi-spectral characteristics, and an effective spectral transmittance of an ink of the printed sample; and
obtaining the optical property of the printed sample based on the estimated effective bi-spectral characteristics.

4. An apparatus for measuring an optical property of a fluorescent sample comprising:
excitation illuminators for illuminating the fluorescent sample by multiple excitation illuminations whose spectral distributions are different from each other in an excitation region of the fluorescent sample;
an analyzer for measuring spectral distributions of the excitation illuminations, and radiations from the fluorescent sample illuminated by the excitation illuminations; and
a processor for controlling the excitation illuminators and the analyzer, and for processing the spectral distributions measured by the analyzer, wherein the processor is operable to illuminate the fluorescent sample by each of the excitation illuminations, measure a spectral distribution of each of the excitation illuminations, and the radiations from the fluorescent sample illuminated by the excitation illuminations, calculate an excitation efficiency of the fluorescent sample illuminated by each of the excitation illuminations based on the measured spectral distributions, calculate ratios between the calculated excitation efficiencies, discriminate the calculated ratios based on predetermined threshold values, select bi-spectral characteristics out of stored multiple bi-spectral characteristics based on the discrimination results, and obtain the optical property of the fluorescent sample based on the selected bi-spectral characteristics.

5. The apparatus for measuring an optical property of a fluorescent sample according to claim 4, further comprising a first illuminator and a second illuminator to be controlled by the processor, and for illuminating the fluorescent sample by a first illumination and a second illumination whose spectral distributions are different from each other, wherein the processor is further operable to illuminate the fluorescent sample by each of the first illumination and the second illumination, measure the spectral distributions of the first illumination and the second illumination, and radiations from the fluorescent sample illuminated by the first illumination and the second illumination, and obtain the optical property of the fluorescent sample, based on a spectral distribution of a predetermined test illumination given in advance, and the selected bi-spectral characteristics.

6. The apparatus for measuring an optical property of a fluorescent sample according to claim 5, wherein for estimating a total spectral radiance factor of the fluorescent sample illuminated by the test illumination, the processor is operable to calculate a first total spectral radiance factor and a second total spectral radiance factor of the fluorescent sample illuminated by the first illumination and the second illumination, respectively, based on the measured spectral distributions of the first illumination, the second illumination, and the radiations from the fluorescent sample illuminated by the first illumination and the second illumination, calculate a first spectral fluorescent characteristic, a second spectral fluorescent characteristic, and a target spectral fluorescent characteristic of the fluorescent sample illuminated by the first illumination, the second illumination, and the test illumination, respectively, based on the selected bi-spectral characteristics, the measured spectral distributions of the first illumination and the second illumination, and the spectral distribution of the test illumination, determine a first weighting factor and a second weighting factor at each fluorescent wavelength so that a linear combination of the first spectral fluorescent characteristic weighted by the first weighting factor, and the second spectral fluorescent characteristic weighted by the second weighting factor match with the target spectral fluorescent characteristic, and calculate a total spectral radiance factor of the fluorescent sample illuminated by the test illumination by linearly combining the first total spectral radiance factor weighted by the first determined weighting factor, and the second total spectral radiance factor weighted by the second determined weighting factor.

7. The apparatus for measuring an optical property of a fluorescent sample according to claim 5, wherein the multiple excitation illuminators are multiple monochromatic light sources whose center wavelengths are different from each other in the excitation region of the fluorescent sample.

8. The apparatus for measuring an optical property of a fluorescent sample according to claim 7, wherein the multiple excitation illuminators are two kinds of LEDs.

9. The apparatus for measuring an optical property of a fluorescent sample according to claim 8, wherein the two kinds of LEDs are a purple LED and a UV LED, and the first illumination and the second illumination are different combinations of output light from the purple LED and the UV LED as the excitation illuminators, and a white LED.

* * * * *